United States Patent
Ulbrandt et al.

(10) Patent No.: US 11,186,628 B2
(45) Date of Patent: *Nov. 30, 2021

(54) RSV-SPECIFIC ANTIBODIES AND FUNCTIONAL PARTS THEREOF

(71) Applicant: MedImmune, LLC, Gaithersburg, MD (US)

(72) Inventors: Nancy Ulbrandt, Gaithersburg, MD (US); Nicole Kallewaard-Lelay, Gaithersburg, MD (US); Andy Q. Yuan, Gaithersburg, MD (US); Bettina Richter, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/864,454

(22) Filed: May 1, 2020

(65) Prior Publication Data

US 2020/0331989 A1    Oct. 22, 2020

Related U.S. Application Data

(63) Continuation of application No. 16/003,455, filed on Jun. 8, 2018, now Pat. No. 10,689,437, which is a continuation of application No. 15/111,610, filed as application No. PCT/US2015/011391 on Jan. 14, 2015, now abandoned.

(60) Provisional application No. 61/927,819, filed on Jan. 15, 2014.

(51) Int. Cl.
   *C07K 16/10*    (2006.01)
   *A61K 39/00*    (2006.01)

(52) U.S. Cl.
   CPC .... *C07K 16/1027* (2013.01); *A61K 2039/505* (2013.01); *C07K 2317/34* (2013.01); *C07K 2317/732* (2013.01); *C07K 2317/76* (2013.01); *C07K 2317/90* (2013.01)

(58) Field of Classification Search
   None
   See application file for complete search history.

(56) References Cited

U.S. PATENT DOCUMENTS

| | | | |
|---|---|---|---|
| 5,807,715 | A | 9/1998 | Morrison et al. |
| 5,892,019 | A | 4/1999 | Schlom et al. |
| 8,092,804 | B2 | 1/2012 | Eriksson et al. |
| 8,562,996 | B2 | 10/2013 | Spits et al. |
| 8,568,726 | B2 | 10/2013 | Beaumont et al. |
| 9,283,274 | B2 | 3/2016 | Beaumont et al. |
| 9,321,831 | B2 | 4/2016 | Spits et al. |
| 10,016,496 | B2 | 7/2018 | Ulbrandt |
| 10,035,843 | B2 | 7/2018 | Beaumont et al. |
| 10,059,757 | B2 | 8/2018 | Spits et al. |
| 2010/0239593 | A1 | 9/2010 | Spits et al. |
| 2011/0008329 | A1 | 1/2011 | Krishnan et al. |
| 2012/0070446 | A1 | 3/2012 | Beaumont et al. |
| 2012/0157662 | A1 | 6/2012 | Beaumont et al. |
| 2012/0263711 | A1 | 10/2012 | Stavenhagen et al. |
| 2012/0263715 | A1 | 10/2012 | Richter et al. |
| 2014/0072575 | A1 | 3/2014 | Spits et al. |
| 2014/0093500 | A1 | 4/2014 | Beaumont et al. |
| 2014/0377279 | A9 | 12/2014 | Spits et al. |
| 2015/0366960 | A1 | 12/2015 | Ulbrandt |
| 2016/0244509 | A1 | 8/2016 | Spits et al. |
| 2016/0251412 | A1 | 9/2016 | Beaumont et al. |
| 2016/0340414 | A1 | 11/2016 | Ulbrandt et al. |

FOREIGN PATENT DOCUMENTS

| | | | |
|---|---|---|---|
| EP | 1997830 | A1 | 12/2008 |
| EP | 3094353 | B1 | 1/2020 |
| JP | 2010-505830 | A | 2/2010 |
| JP | 2010-528601 | A | 8/2010 |
| WO | WO 2006/050166 | A2 | 5/2006 |
| WO | WO 2006050166 | A3 | 11/2006 |
| WO | WO 2008/060367 | A2 | 5/2008 |
| WO | WO 2008106980 | A2 | 9/2008 |
| WO | WO 2008/147196 | A2 | 12/2008 |
| WO | WO 2009003019 | A1 | 12/2008 |
| WO | WO 2011/043643 | A1 | 4/2011 |
| WO | WO 2013/136193 | A2 | 9/2013 |
| WO | WO 2013/177264 | A1 | 11/2013 |
| WO | WO 2014/121021 | A1 | 8/2014 |
| WO | WO 2015/108967 | A2 | 7/2015 |
| WO | WO 2015/108967 | A3 | 9/2015 |
| WO | WO 2018/158332 | A1 | 9/2018 |
| WO | WO 2018/160722 | A1 | 9/2018 |

OTHER PUBLICATIONS

Rudikoff et al., Proc Natl Acad Sci USA vol. 79 p. 1979 (Year: 1982).*
MacCallum et al.,. J. Mol. Biol. vol. 262, 732-745 (Year: 1996).*
U.S. Appl. No. 15/111,610, filed Jul. 14, 2016, MedImmune, LLC.
U.S. Appl. No. 15/907,876, filed Feb. 28, 2018, MedImmune, Ltd.
U.S. Appl. No. 16/003,455, filed Jun. 8, 2018, MedImmune, LLC.
U.S. Appl. No. 16/042,547, filed Jul. 23, 2018, Spits et al.
U.S. Appl. No. 16/047,524, filed. Jul. 27, 2018, Beaumont et al.
"AIMM Therapeutics' Partner MedImmune Starts Clinical Studies with RSV Antibody." Press Release [online]. AIMM Therapeutics, Jul. 2, 2014. [retrieved May 17, 2017]. Retrieved from the Internet:http://www.aimmtherapeutics.com/news-and-events/2014/medimmune-starts-clinical-studies/ (2 pages).
Beeler et al., "Neutralization Epitopes of the F Glycoprotein of Respiratory Syncytial Virus: Effect of Mutation Upon Fusion Function," *Journal of Virology*, 1989; 63(7):2941-2950.

(Continued)

*Primary Examiner* — Shanon A. Foley
*Assistant Examiner* — Myron G Hill
(74) *Attorney, Agent, or Firm* — Finnegan, Henderson, Farabow, Garrett & Dunner, LLP

(57) ABSTRACT

This application provides antibodies and functional equivalents thereof which are capable of specifically binding RSV, as well as means and methods for producing them.

11 Claims, 12 Drawing Sheets

Specification includes a Sequence Listing.

(56) References Cited

OTHER PUBLICATIONS

Bitter et al., "Expression and Secretion Vectors for Yeast," *Methods in Enzymology*, 1987; 153:516-544.
Cockett et al., "High Level Expression of Tissue Inhibitor of Metalloproteinases in Chinese Hamster Ovary Cells Using Glutamine Synthetase Gene Amplification," *Biotechnology* (now *Nature Biotechnology*), 1990; 8(7):662-667.
Colbère-Garapin et al., "A New Dominant Hybrid Selective Marker for Higher Eukaryotic Cells," *Journal of Molecular Biology*, 1981; 150(1):1-14.
Dall'Acqua et al., "Properties of Human IgG1s Engineered for Enhanced Binding to the Neonatal Fc Receptor (FcRn)," *The Journal of Biological Chemistry*, 2006; 281(33):23514-23524.
Diamond et. al., "Somatic mutation of the T15 heavy chain gives rise to an antibody with autoantibody specificity," Sep. 1984 *Proc. Natl. Acad. Sci. USA*, vol. 81: 5841-5844.
Foecking et al., "Powerful and Versatile Enhancer-Promoter Unit for Mammalian Expression Vectors," *Gene*, 1986; 45(1):101-105.
Griffin et al., "Safety, Tolerability, and Pharmacokinetics of MEDI8897, the Respiratory Syncytial Virus Prefusion F-Targeting Monoclonal Antibody with an Extended Half-Life, in Healthy Adults," *Antimicrobial Agents and Chemotherapy*, Mar. 2017; 61(3):e01714-e01716. Accepted manuscript posted online Dec. 12, 2016.
Inouye et al., "Up-promoter Mutations in the lpp Gene of *Escherichia coli*," *Nucleic Acids Research*, 1985; 13(9):3101-3110.
Kwakkenbos et al., "Generation of Stable Monoclonal Antibody-Producing BCR+ Human Memory B Cells by Genetic Programming," *Nature Medicine*, Jan. 2010; 16(1): 123-128. Author manuscript available in PMC Jul. 1, 2010.
Logan et al., "Adenovirus Tripartite Leader Sequence Enhances Translation of mRNAs Late After Infection," *Proc. Natl. Acad. Sci. USA*, 1984; 81:3655-3659.
Lowy et al., "Isolation of Transforming DNA: Cloning the Hamster aprt Gene," *Cell*, 1980; 22(3):817-823.
McLellan et al., "Structure of RSV Fusion Glycoprotein Trimer Bound to a Prefusion-Specific Neutralizing Antibody," *Science*, 2013; 340(6136):1113-1117.
Mejias et al., "Comparative Effects of Two Neutralizing Anti-Respiratory Syncytial Virus (RSV) Monoclonal Antibodies in the RSV Murine Model: Time Versus Potency," *Antimicrobial Agents and Chemotherapy*, 2005, vol. 49, No. 11, pp. 4700-4707.
Morgan et al., "Human Gene Therapy," *Annual Review of Biochemistry*, 1993; 62:191-217.
Mulligan et al., "Selection for Animal Cells that Express the *Escherichia coli* Gene Coding for Xanthine-Guanine Phosphoribosyltransferase," *Proc. Natl. Aca. Sci. USA*, 1981; 78(4):2072-2076.
Mulligan, "The Basic Science of Gene Therapy," *Science*, 1993; 260(5110):926-932.
O'Hare et al., "Transformation of Mouse Fibroblasts to Methotrexate Resistance by a Recombinant Plasmid Expressing a Prokaryotic Dihydrofolate Reductase," *Proc. Natl. Acad. Sci USA*, 1981; 78(3):1527-1531.
Ohno et. al., "Antigen-binding specificities of antibodies are primarily determined by seven residues of VH," May 1985 *Proc. Natl. Acad. Sci. USA*, vol. 82: 2945-2949.
Robbie, et al., "A Novel Investigational Fc-Modified Humanized Monoclonal Antibody, Motavizumab-YTE, has an Extended Half-Life in Healthy Adults," *Antimicrobial Agents and Chemotherapy*, Dec. 2013, 57(12):6147-6153. Published ahead of print Sep. 30, 2013.
Rudikoff et al., "Single amino acid substitution of altering antigen-binding specificity," Mar. 1982 *Proc. Nat. Acad. Sci. USA. Immunology*, vol. 79: 1979-1983.
Rüther et al., "Easy Identification of cDNA Clones," *The EMBO Journal*, 1983; 2(10):1791-1794.
Santerre et al., "Expression of Prokaryotic genes for Hygromycin B and G418 Resistance as Dominant-Selection markers in Mouse L Cells," *Gene*, 1984; 30(13)147-156.

Sela-Culang, "The Structural Basis of Antibody-Antigen Recognition," *Frontiers in Immunology*, 2013; 4:1-13.
Szybalska et al, "Genetics of Human Cell Lines, IV. DNA-Mediated Heritable Transformation of a Biochemical Trait," *Proc. Natl. Acad. Sci. USA*, 1962; 48(12):2026-2034.
Tolstoshev, "Gene therapy, concepts, current trials and future directions," Annu Rev Pharmacol Toxicol. 1993; 32:573-96.
Van Heeke et al., "Expression of Human Asparagine Synthetase in *Escherichia coli*," *Journal of Biological Chemistry*, 1989; 264(10):5503-5509.
Wigler et al., "Transformation of Mammalian Cells with an Amplifiable Dominant-Acting Gene," *Proc. Natl. Acad. Sci. USA*, 1980; 77(6):3567-3570.
Wigler et al., "Transfer of Purified Herpes Virus Thymidine Kinase Gene to Cultured Mouse Cells," *Cell*, 1977; 11(1):223-232.
Wu et al., "Delivery Systems for Gene Therapy," *Biotherapy*, 1991; 3(1):87-95.
Wu et al., "Ultra-Potent Antibodies Against Respiratory Syncytial Virus: Effects of Binding Kinetics and Binding Valence on Viral Neutralization," *Journal of Molecular Biol.*, 2005, vol. 350, No. 1, pp. 126-144.
Yarlin, "Osnovy immunologii," 1999 *M.: Medicine*, pp. 172-174.
Zhu et al., "A Highly Potent Extended Half-Life Antibody as a Potential RSV Vaccine Surrogate for all Infants," *Science Translational Medicine*, May 3, 2017; vol. 9, with supplementary materials; 27 pages.
European Patent Application No. 15737068.5, Search Report dated Aug. 8, 2017; 8 pages.
European Patent Application No. 15737068.5, Office Action dated Jul. 30, 2018; 5 pages.
Information Disclosure Statement Transmittal Letter, dated Dec. 20, 2018, signed by Nancy A. Johnson; 3 pages.
International Search Report and Written Opinion for PCT Application No. PCT/US2015/011391, dated Jul. 10, 2015, 12 pages.
Japanese Patent Application No. 2016-541720, Notice of Reasons for Rejection, dated Nov. 27, 2018, with English translation; 7 pages.
Russian Patent Application No. 2016133247, Office Action dated Aug. 22, 2018, with English translation; 7 pages.
Information Disclosure Statement Transmittal Letter filed Dec. 20, 2018, for U.S. Appl. No. 16/003,455; 4 pages.
U.S. Office Action dated Mar. 18, 2019, for U.S. Appl. No. 16/003,455; 13 pages.
Applicant-Initiated Interview Summary dated Jun. 10, 2019, for U.S. Patent Appl. No. 16/003,455; 6 pages.
Amendment and Response filed Aug. 1, 2019, for U.S. Appl. No. 16/003,455; 22 pages.
Ex parte Quayle Action issued Oct. 21, 2019, for U.S. Appl. No. 16/003,455; 7 pages.
Petition filed Dec. 29, 2019, for U.S. Appl. No. 16/003,455; 6 pages.
Petition Decision dated Mar. 5, 2020, for U.S. Appl. No. 16/003,455; 4 pages.
Amendment and Response filed Mar. 19, 2020, for U.S. Appl. No. 16/003,455; 8 pages.
Decision to Grant a European Patent Pursuant to Article 97(1) EPC dated Mar. 5, 2020, for EP Patent Application No. 15737068.5; 2 pages.
Choi, "Antibodies to the Central Conserved Region of Respiratory Syncytial Virus (RSV) G Protein Block RSV G Protein CX3C-CX3CR1 Binding and Cross-Neutralize RSV A and B Strains" Feb. 2012, *Viral Immunology*, 25(3):193-203.
European Patent Application No. 20161884.0, filed Mar. 9, 2020; Extended Search Report dated Oct. 26, 2020; 10 pages.
Information Disclosure Statement Transmittal Letter, dated Jul. 9, 2021, signed by Nancy A. Johnson; 3 pages.
Frankel et al., "Characterization of diphtheria fusion proteins targeted to the human interleukin-3 receptor," *Protein Engineering*, 2000, 13(8):575-581.
Pakula et al., "Genetic analysis of protein stability and function," *Annual Review of Genetics*, 1989, 23(1):289-310.

(56) References Cited

OTHER PUBLICATIONS

Witkowski et al. "Conversion of a beta-Ketoacyl Synthase to a Malonyl Decarboxylase by Replacement of the Active-Site Cysteine with Glutamine," *Biochemistry*, 1999, 38:11643-11650.

* cited by examiner

Fig. 1A

D25 Heavy Chain Sequence

```
         *        *   ***       *        *
QVQLVQSGAEVKKPGSSVMVSCQASGGPLRNYIINWLRQAPGQGPEWMGGIIPVLGTVHY
      *   *        *       *              *
APKFQGRVTITADESTDTAYIHLISLRSEDTAMYYCATETALVVSTTYLPHYFDNWGQGT
LVTVSS (SEQ ID NO: 7)
```

- CDRs underlined in D25
- Nongermline residues indicated by * above
- Residues switched back to germline indicated by ^ above

J Variant

```
         *    *   ***       *        *
QVQLVQSGAEVKKPGSSVMVSCQASGGPLRNYIINWVRQAPGQGPEWMGGIIPVLGTVHY
      *   *        *   ^^   *              *
APKFQGRVTITADESTDTAYMELSSLRSEDTAMYYCATETALVVSTTYLPHYFDNWGQGT
LVTVSS (SEQ ID NO: 12)
```

Fig. 1B

L Variant

QVQLVQSGAEVKKPGSSVMVSCQASGGPLRNYIINWVRQAPGQGLEWMGGIIPVLGTVHY
APKFQGRVTITADESTDTAYMELSSLRSEDTAMYYCATETALVVSTTYLPHYFDNWGQGT
LVTVSS (SEQ ID NO: 13)

LA Variant

QVQLVQSGAEVKKPGSSVKVSCKASGGTFSNYIINWVRQAPGQGLEWMGGIIPVLGTVHY
APKFQGRVTITADESTDTAYMELSSLRSEDTAMYYCATETALVVSTTYLPHYFDNWGQGT
LVTVSS (SEQ ID NO: 14)

Fig. 2

Optimized Variants

1G7
```
                *            *          #*##          *^
QVQLVQSGAEVKKPGSSVMVSCQASGGLLEDYIINWVRQAPGQGPEWMGGIIPVLGTV
       *            ^^  ^                   *
HYGPKFQGRVTITADESTDTAYMELSSLRSEDTAMYYCATETALVVSETYLPHYFDNW

GQGTLVTVSS (SEQ ID NO: 23)
```

1F5
```
                *            *          **##         ^
QVQLVQSGAEVKKPGSSVMVSCQASGGPLEDYIINWVRQAPGQGPEWMGGIIPVLGTV
       *            ^^  ^                   *
HYGPKFQGRVTITADESTDTAYMELSSLRSEDTAMYYCATETALVVSTTYLPHYFDNW

GQGTLVTVSS (SEQ ID NO: 16)
```

2D10
```
                *            *          **##         ^
QVQLVQSGAEVKKPGSSVMVSCQASGGPLEDYIINWVRQAPGQGPEWMGGIIPVLGTV
       *            ^^  ^                   *        #
HYGPKFQGRVTITADESTDTAYMELSSLRSEDTAMYYCATETALVVSTTYRPHYFDNW

GQGTLVTVSS (SEQ ID NO: 17)
```

Residues with * above are the non-germline residues
Residues with ^ above are the switched back to germline residues
Residues with # above are changes that increase activity in vitro

Fig. 3A

1G7-GLM (pI 7.31)

QVQLVQSGAEVKKPGSSVKVSCKASGGLLEDYIINWVRQAPGQGPEWMGGIIPVLG
TVHYGPKFQGRVTITADESTSTAYMHLSSLRSEDTAMYYCARETALVVSTTYLPHY
FDNWGQGTLVTVSS (SEQ ID NO: 18)

B12-1 (pI 6.97)

QVQLVQSGAEVKKPGSSVKVSCKASGGLLEDYIINWVRQAPGQGPEWMGGIIPVLG
TVHYGPKFQGRVTITADESTDTAYMHLSSLRSEDTAMYYCATETALVVSTTYLPHY
FDNWGQGTLVTVSS (SEQ ID NO: 19)

Residues designated with ~ above represent modifications made to 1G7 to alter pI by incorporating germline residues

QVQLVQSGAEVKKPGSSVKVSCKASGGLLEDYIINWVRQAPGQGPEWMGGIIPVLG
TVHYGPKFQGRVTITADESTSTAYMELSSLRSEDTAMYYCATETALVVSTTYLPHY
FDNWGQGTLVTVSS (SEQ ID NO: 20)

E9-2 (pI 7.13)

QVQLVQSGAEVKKPGSSVKVSCKASGGLLEDYIINWVRQAPGQGPEWMGGIIPVLG
TVHYGPKFQGRVTITADESTSTAYMHLSSLRSEDTAMYYCATETALVVSTTYLPHY
FDNWGQGTLVTVSS (SEQ ID NO: 21)

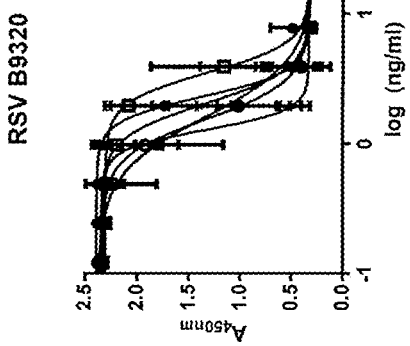
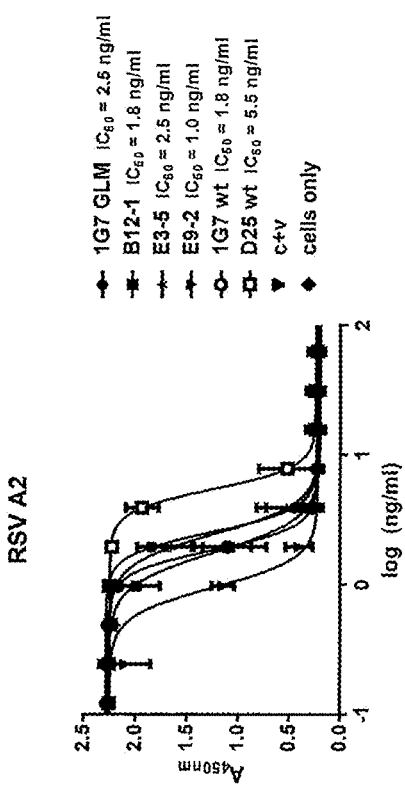
Fig. 8A
Fig. 8B

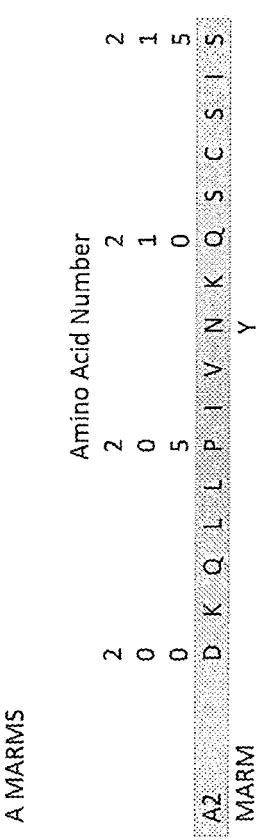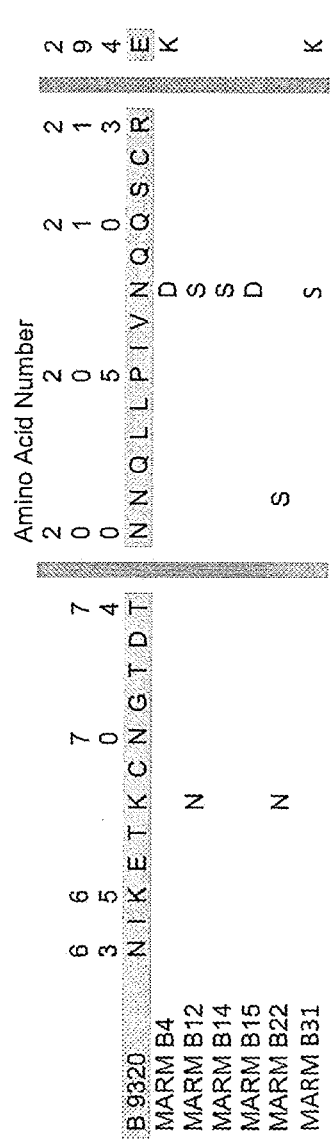
Fig. 9A
Fig. 9B

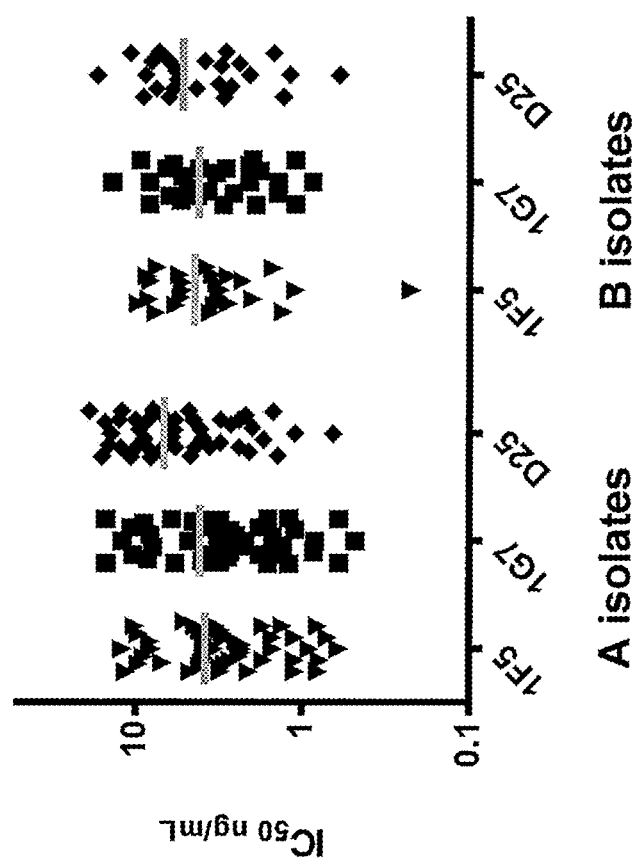

```
                        SEQUENCE LISTING

<160> NUMBER OF SEQ ID NOS: 23

<210> SEQ ID NO 1
    <211> LENGTH: 5
    <212> TYPE: PRT
    <213> ORGANISM: artificial
    <220> FEATURE:
    <223> OTHER INFORMATION: D25 Heavy Chain CDR1

<400> SEQUENCE: 1

Asn Tyr Ile Ile Asn
    1               5

<210> SEQ ID NO 2
    <211> LENGTH: 17
    <212> TYPE: PRT
    <213> ORGANISM: artificial
    <220> FEATURE:
    <223> OTHER INFORMATION: D25 Heavy Chain CDR2

<400> SEQUENCE: 2

Gly Ile Ile Pro Val Leu Gly Thr Val His Tyr Ala Pro Lys Phe Gln
    1               5                   10                  15

Gly

<210> SEQ ID NO 3
    <211> LENGTH: 17
    <212> TYPE: PRT
    <213> ORGANISM: artificial
    <220> FEATURE:
    <223> OTHER INFORMATION: D25 Heavy Chain CDR3

<400> SEQUENCE: 3

Glu Thr Ala Leu Val Val Ser Thr Thr Tyr Leu Pro His Tyr Phe Asp
    1               5                   10                  15

Asn

<210> SEQ ID NO 4
```

```
<211> LENGTH: 11
<212> TYPE: PRT
<213> ORGANISM: artificial
<220> FEATURE:
<223> OTHER INFORMATION: D25 Light Chain CDR1

<400> SEQUENCE: 4

Gln Ala Ser Gln Asp Ile Val Asn Tyr Leu Asn
1               5                   10

<210> SEQ ID NO 5
<211> LENGTH: 7
<212> TYPE: PRT
<213> ORGANISM: artificial
<220> FEATURE:
<223> OTHER INFORMATION: D25 Light Chain CDR2

<400> SEQUENCE: 5

Val Ala Ser Asn Leu Glu Thr
1               5

<210> SEQ ID NO 6
<211> LENGTH: 7
<212> TYPE: PRT
<213> ORGANISM: artificial
<220> FEATURE:
<223> OTHER INFORMATION: D25 Light Chain CDR3

<400> SEQUENCE: 6

Gln Gln Tyr Asp Asn Leu Pro
1               5

<210> SEQ ID NO 7
<211> LENGTH: 126
<212> TYPE: PRT
<213> ORGANISM: artificial
<220> FEATURE:
<223> OTHER INFORMATION: D25 heavy chain variable region

<400> SEQUENCE: 7

Gln Val Gln Leu Val Gln Ser Gly Ala Glu Val Lys Lys Pro Gly Ser
1               5                   10                  15

Ser Val Met Val Ser Cys Gln Ala Ser Gly Gly Pro Leu Arg Asn Tyr
                20                  25                  30

Ile Ile Asn Trp Leu Arg Gln Ala Pro Gly Gln Gly Pro Glu Trp Met
            35                  40                  45

Gly Gly Ile Ile Pro Val Leu Gly Thr Val His Tyr Ala Pro Lys Phe
    50                  55                  60

Gln Gly Arg Val Thr Ile Thr Ala Asp Glu Ser Thr Asp Thr Ala Tyr
65                  70                  75                  80

Ile His Leu Ile Ser Leu Arg Ser Glu Asp Thr Ala Met Tyr Tyr Cys
                85                  90                  95

Ala Thr Glu Thr Ala Leu Val Val Ser Thr Tyr Tyr Leu Pro His Tyr
                100                 105                 110

Phe Asp Asn Trp Gly Gln Gly Thr Leu Val Thr Val Ser Ser
            115                 120                 125

<210> SEQ ID NO 8
<211> LENGTH: 110
<212> TYPE: PRT
<213> ORGANISM: artificial
<220> FEATURE:
<223> OTHER INFORMATION: D25 light chain variable region
```

<400> SEQUENCE: 8

Asp Ile Gln Met Thr Gln Ser Pro Ser Leu Ser Ala Ala Val Gly
1               5                   10                  15

Asp Arg Val Thr Ile Thr Cys Gln Ala Ser Gln Asp Ile Val Asn Tyr
            20                  25                  30

Leu Asn Trp Tyr Gln Gln Lys Pro Gly Lys Ala Pro Lys Leu Leu Ile
        35                  40                  45

Tyr Val Ala Ser Asn Leu Glu Thr Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys Arg Thr Val
            100                 105                 110

<210> SEQ ID NO 9
<211> LENGTH: 5
<212> TYPE: PRT
<213> ORGANISM: artificial
<220> FEATURE:
<223> OTHER INFORMATION: Alternative Heavy Chain CDR1

<400> SEQUENCE: 9

Asp Tyr Ile Ile Asn
1               5

<210> SEQ ID NO 10
<211> LENGTH: 17
<212> TYPE: PRT
<213> ORGANISM: artificial
<220> FEATURE:
<223> OTHER INFORMATION: Alternative Heavy Chain CDR2

<400> SEQUENCE: 10

Gly Ile Ile Pro Val Leu Gly Thr Val His Tyr Gly Pro Lys Phe Gln
1               5                   10                  15

Gly

<210> SEQ ID NO 11
<211> LENGTH: 17
<212> TYPE: PRT
<213> ORGANISM: artificial
<220> FEATURE:
<223> OTHER INFORMATION: Alternative Heavy Chain CDR3

<400> SEQUENCE: 11

Glu Thr Ala Leu Val Val Ser Thr Thr Tyr Arg Pro His Tyr Phe Asp
1               5                   10                  15

Asn

<210> SEQ ID NO 12
<211> LENGTH: 126
<212> TYPE: PRT
<213> ORGANISM: artificial
<220> FEATURE:
<223> OTHER INFORMATION: J variant heavy chain variable region

<400> SEQUENCE: 12

Gln Val Gln Leu Val Gln Ser Gly Ala Glu Val Lys Lys Pro Gly Ser
1               5                   10                  15

```
Ser Val Met Val Ser Cys Gln Ala Ser Gly Gly Pro Leu Arg Asn Tyr
            20                  25                  30

Ile Ile Asn Trp Val Arg Gln Ala Pro Gly Gln Gly Pro Glu Trp Met
        35                  40                  45

Gly Gly Ile Ile Pro Val Leu Gly Thr Val His Tyr Ala Pro Lys Phe
    50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110

Phe Asp Asn Trp Gly Gln Gly Thr Leu Val Thr Val Ser Ser
        115                 120                 125

<210> SEQ ID NO 13
<211> LENGTH: 126
<212> TYPE: PRT
<213> ORGANISM: artificial
<220> FEATURE:
<223> OTHER INFORMATION: L variant heavy chain variable region

<400> SEQUENCE: 13

Gln Val Gln Leu Val Gln Ser Gly Ala Glu Val Lys Lys Pro Gly Ser
1               5                   10                  15

Ser Val Met Val Ser Cys Gln Ala Ser Gly Gly Pro Leu Arg Asn Tyr
            20                  25                  30

Ile Ile Asn Trp Val Arg Gln Ala Pro Gly Gln Gly Leu Glu Trp Met
        35                  40                  45

Gly Gly Ile Ile Pro Val Leu Gly Thr Val His Tyr Ala Pro Lys Phe
    50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110

Phe Asp Asn Trp Gly Gln Gly Thr Leu Val Thr Val Ser Ser
        115                 120                 125

<210> SEQ ID NO 14
<211> LENGTH: 126
<212> TYPE: PRT
<213> ORGANISM: artificial
<220> FEATURE:
<223> OTHER INFORMATION: LA variant heavy chain variable region

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ile Ile Asn Trp Val Arg Gln Ala Pro Gly Gln Gly Leu Glu Trp Met
        35                  40                  45

Gly Gly Ile Ile Pro Val Leu Gly Thr Val His Tyr Ala Pro Lys Phe
    50                  55                  60

Gln Gly Arg Val Thr Ile Thr Ala Asp Glu Ser Thr Asp Thr Ala Tyr
65                  70                  75                  80
```

Met Glu Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110

Phe Asp Asn Trp Gly Gln Gly Thr Leu Val Thr Val Ser Ser
            115                 120                 125

<210> SEQ ID NO 15
<211> LENGTH: 126
<212> TYPE: PRT
<213> ORGANISM: artificial
<220> FEATURE:
<223> OTHER INFORMATION: 1G7 heavy chain variable region

<400> SEQUENCE: 15

Gln Val Gln Leu Val Gln Ser Gly Ala Glu Val Lys Lys Pro Gly Ser
1               5                   10                  15

Ser Val Met Val Ser Cys Gln Ala Ser Gly Gly Leu Leu Glu Asp Tyr
            20                  25                  30

Ile Ile Asn Trp Val Arg Gln Ala Pro Gly Gln Gly Pro Glu Trp Met
        35                  40                  45

Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110

Phe Asp Asn Trp Gly Gln Gly Thr Leu Val Thr Val Ser Ser
            115                 120                 125

<210> SEQ ID NO 16
<211> LENGTH: 126
<212> TYPE: PRT
<213> ORGANISM: artificial
<220> FEATURE:
<223> OTHER INFORMATION: 1F5 heavy chain variable region

<400> SEQUENCE: 16

Gln Val Gln Leu Val Gln Ser Gly Ala Glu Val Lys Lys Pro Gly Ser
1               5                   10                  15

Ser Val Met Val Ser Cys Gln Ala Ser Gly Gly Pro Leu Glu Asp Tyr
            20                  25                  30

Ile Ile Asn Trp Val Arg Gln Ala Pro Gly Gln Gly Pro Glu Trp Met
        35                  40                  45

Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110

Phe Asp Asn Trp Gly Gln Gly Thr Leu Val Thr Val Ser Ser
            115                 120                 125

```
<210> SEQ ID NO 17
<211> LENGTH: 126
<212> TYPE: PRT
<213> ORGANISM: artificial
<220> FEATURE:
<223> OTHER INFORMATION: 2D10 heavy chain variable region

<400> SEQUENCE: 17

Gln Val Gln Leu Val Gln Ser Gly Ala Glu Val Lys Lys Pro Gly Ser
1               5                   10                  15

Ser Val Met Val Ser Cys Gln Ala Ser Gly Gly Pro Leu Glu Asp Tyr
                20                  25                  30

Ile Ile Asn Trp Val Arg Gln Ala Pro Gly Gln Gly Pro Glu Trp Met
            35                  40                  45

Gly Gly Ile Ile Pro Val Leu Gly Thr Val His Tyr Gly Pro Lys Phe
50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Thr Thr Tyr Arg Pro His Tyr
            100                 105                 110

Phe Asp Asn Trp Gly Gln Gly Thr Leu Val Thr Val Ser Ser
        115                 120                 125

<210> SEQ ID NO 18
<211> LENGTH: 126
<212> TYPE: PRT
<213> ORGANISM: artificial
<220> FEATURE:
<223> OTHER INFORMATION: 1G7-GLM heavy chain variable region

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Leu Leu Glu Asp Tyr
                20                  25                  30

Ile Ile Asn Trp Val Arg Gln Ala Pro Gly Gln Gly Pro Glu Trp Met
            35                  40                  45

Gly Gly Ile Ile Pro Val Leu Gly Thr Val His Tyr Gly Pro Lys Phe
50                  55                  60

Gln Gly Arg Val Thr Ile Thr Ala Asp Glu Ser Thr Ser Thr Ala Tyr
65                  70                  75                  80

Met His Leu Ser Ser Leu Arg Ser Glu Asp Thr Ala Met Tyr Tyr Cys
                85                  90                  95

Ala Arg Glu Thr Ala Leu Val Val Ser Thr Thr Tyr Leu Pro His Tyr
            100                 105                 110

Phe Asp Asn Trp Gly Gln Gly Thr Leu Val Thr Val Ser Ser
        115                 120                 125

<210> SEQ ID NO 19
<211> LENGTH: 126
<212> TYPE: PRT
<213> ORGANISM: artificial
<220> FEATURE:
<223> OTHER INFORMATION: B12-1 heavy chain variable region

<400> SEQUENCE: 19

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Leu Leu Glu Asp Tyr
            20                  25                  30

Ile Ile Asn Trp Val Arg Gln Ala Pro Gly Gln Gly Pro Glu Trp Met
            35                  40                  45

Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Asp Thr Ala Tyr
65                  70                  75                  80

Met His Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
                100                 105                 110

Phe Asp Asn Trp Gly Gln Gly Thr Leu Val Thr Val Ser Ser
            115                 120                 125

<210> SEQ ID NO 20
<211> LENGTH: 126
<212> TYPE: PRT
<213> ORGANISM: artificial
<220> FEATURE:
<223> OTHER INFORMATION: E3-5 heavy chain variable region

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Leu Leu Glu Asp Tyr
            20                  25                  30

Ile Ile Asn Trp Val Arg Gln Ala Pro Gly Gln Gly Pro Glu Trp Met
            35                  40                  45

Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
                100                 105                 110

Phe Asp Asn Trp Gly Gln Gly Thr Leu Val Thr Val Ser Ser
            115                 120                 125

<210> SEQ ID NO 21
<211> LENGTH: 126
<212> TYPE: PRT
<213> ORGANISM: artificial
<220> FEATURE:
<223> OTHER INFORMATION: E9-2 heavy chain variable region

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Leu Leu Glu Asp Tyr
            20                  25                  30

Ile Ile Asn Trp Val Arg Gln Ala Pro Gly Gln Gly Pro Glu Trp Met
            35                  40                  45

Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Ser Thr Ala Tyr
```

65 70 75 80
Met His Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
               100                 105                 110

Phe Asp Asn Trp Gly Gln Gly Thr Leu Val Thr Val Ser Ser
           115                 120                 125

<210> SEQ ID NO 22
<211> LENGTH: 17
<212> TYPE: PRT
<213> ORGANISM: Artificial
<220> FEATURE:
<223> OTHER INFORMATION: Alternative Heavy Chain CDR3

<400> SEQUENCE: 22

Glu Thr Ala Leu Val Val Ser Glu Thr Tyr Leu Pro His Tyr Phe Asp
1               5                   10                  15
Asn

<210> SEQ ID NO 23
<211> LENGTH: 126
<212> TYPE: PRT
<213> ORGANISM: Artificial
<220> FEATURE:
<223> OTHER INFORMATION: 1G7 heavy chain variable region

<400> SEQUENCE: 23

Gln Val Gln Leu Val Gln Ser Gly Ala Glu Val Lys Lys Pro Gly Ser
1               5                   10                  15

Ser Val Met Val Ser Cys Gln Ala Ser Gly Gly Leu Leu Glu Asp Tyr
                20                  25                  30

Ile Ile Asn Trp Val Arg Gln Ala Pro Gly Gln Gly Pro Glu Trp Met
            35                  40                  45

Gly Gly Ile Ile Pro Val Leu Gly Thr Val His Tyr Gly Pro Lys Phe
        50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Glu Thr Tyr Leu Pro His Tyr
               100                 105                 110

Phe Asp Asn Trp Gly Gln Gly Thr Leu Val Thr Val Ser Ser
           115                 120                 125

RSV-SPECIFIC ANTIBODIES AND FUNCTIONAL PARTS THEREOF

CONTINUING APPLICATION DATA

This application is a continuation of U.S. patent application Ser. No. 16/003,455, filed Jun. 8, 2018, which is a continuation of U.S. patent application Ser. No. 15/111,610, filed Jul. 14, 2016, which is the § 371 U.S. National Stage of International Application No. PCT/US2015/011391, filed Jan. 15, 2015, which claims the benefit of U.S. Provisional Application Ser. No. 61/927,819, filed Jan. 15, 2014, each of which is incorporated by reference herein.

SEQUENCE LISTING

This application contains a Sequence Listing electronically submitted via EFS-Web to the United States Patent and Trademark Office as an ASCII text file entitled "RSVNG-103US3_ST25.txt" having a size of 18 kilobytes and created on Nov. 4, 2020. The information contained in the Sequence Listing is incorporated by reference herein.

DESCRIPTION

Field

This application relates to the field of biotechnology and medicine.

Background

Respiratory Syncytial Virus (RSV) is a common cold virus belonging to the family of paramyxovirus. RSV is virulent, easily transmissible and the most common cause of lower respiratory tract disease in children of less than 2 years of age. Up to 98% of children attending day care will be infected in a single RSV season. Between 0.5% and 3.2% of children with RSV infection require hospitalization. Approximately 90,000 hospital admissions and 4,500 deaths per year were reported in United States. Major risk factors for hospitalization due to RSV are premature birth, chronic lung disease, congenital heart disease, compromised immunity, and age younger than 6 weeks in otherwise healthy children. There is a need for additional treatment for RSV positive bronchiolitis beside supportive care in the form of adequate nutrition and oxygen therapy. Antiviral therapies such as Ribavirin have not been proven to be effective in RSV infection. One monoclonal antibody, Palivizumab (also called Synagis®), is registered for prophylaxis against RSV infection. Palivizumab is a genetically engineered (humanized) monoclonal antibody to the fusion protein of RSV. While Palivizumab has been a very effective prophylactic, alternative antibodies and therapies providing additional coverage against RSV would be advantageous.

It is an object to provide means and methods for counteracting and/or preventing an RSV infection. It is a further object to provide alternative and/or improved antibodies against RSV, or functional equivalents of such antibodies, and to provide stable cells capable of producing antibodies or functional equivalents thereof against RSV.

SUMMARY

In accordance with the description, a synthetic, recombinant, or isolated antibody or a functional part thereof capable of specifically binding Respiratory Syncytial Virus comprises:

a. a heavy chain variable region CDR1 sequence comprising a sequence which is at least 70% identical to the sequence NYIIN (SEQ ID NO: 1) or DYIIN (SEQ ID NO: 9), and b. a heavy chain variable region CDR2 sequence comprising a sequence which is at least 75% identical to the sequence GIIPVLGTVHYAPKFQG (SEQ ID NO: 2) or GIIPVLGTVHYGPKFQG (SEQ ID NO: 10), and c. a heavy chain variable region CDR3 sequence comprising a sequence which is at least 70% identical to the sequence ETALVVSTTYLPHYFDN (SEQ ID NO: 3) or ETALVVSTTYRPHYFDN (SEQ ID NO: 11), and d. a light chain variable region CDR1 sequence comprising a sequence which is at least 85% identical to the sequence QASQDIVNYLN (SEQ ID NO: 4), and e. a light chain variable region CDR2 sequence comprising a sequence which is at least 70% identical to the sequence VASNLET (SEQ ID NO: 5), and f. a light chain variable region CDR3 sequence comprising a sequence which is at least 70% identical to the sequence QQYDNLP (SEQ ID NO: 6).

and wherein at least one amino acid in the heavy chain differs from SEQ ID NO: 7 and said at least one amino acid is chosen from:

| Position relative to SEQ ID NO: 1 | Amino Acid |
| --- | --- |
| 19 | K |
| 23 | K |
| 28 | T or L |
| 29 | F |
| 30 | S or E |
| 37 | V |
| 45 | L |
| 77 | S |
| 81 | M |
| 82 | E or H |
| 84 | S |
| 98 | R |

In another embodiment, the antibody or functional part comprises:

a. heavy chain variable region CDR1 sequence comprises a sequence which differs by one amino acid from NYIIN (SEQ ID NO: 1) or DYIIN (SEQ ID NO: 9), b. heavy chain variable region CDR2 sequence comprises a sequence which differs by one or two amino acids from GIIPVLGTVHYAPKFQG (SEQ ID NO: 2) or GIIPVLGTVHYGPKFQG (SEQ ID NO: 10), c. heavy chain variable region CDR3 sequence comprises a sequence which differs by one or two amino acid from ETALVVSTTYLPHYFDN (SEQ ID NO: 3) or ETALVVSTTYRPHYFDN (SEQ ID NO: 11), d. light chain variable region CDR1 sequence comprises a sequence which differs by one amino acid from QASQDIVNYLN (SEQ ID NO: 4), e. light chain variable region CDR2 sequence comprises a sequence which differs by one amino acid from VASNLET (SEQ ID NO: 5), and/or f. light chain variable region CDR3 sequence comprises a sequence which differs by one amino acid from QQYDNLP (SEQ ID NO: 6).

In another embodiment, the antibody or functional part comprises a. heavy chain variable region CDR1 sequence comprises NYIIN (SEQ ID NO: 1) or DYIIN (SEQ ID NO: 9), b. heavy chain variable region CDR2 sequence comprises GIIPVLGTVHYAPKFQG (SEQ ID NO: 2) or GIIPVLGTVHYGPKFQG (SEQ ID NO: 10),
c. heavy chain variable region CDR3 sequence comprises ETALVVSTTYLPHYFDN (SEQ ID NO: 3) or ETALVVSTTYRPHYFDN (SEQ ID NO: 11),
d. light chain variable region CDR1 sequence comprises QASQDIVNYLN (SEQ ID NO: 4),
e. light chain variable region CDR2 sequence comprises VASNLET (SEQ ID NO: 5), and
f. light chain variable region CDR3 sequence comprises QQYDNLP (SEQ ID NO: 6).

In a further embodiment, the antibody or functional part comprises at least the following amino acids in the heavy chain variable region that differ from SEQ ID NO: 7:

| Position relative to SEQ ID NO: 7 | Amino Acid |
|---|---|
| 28 | L |
| 30 | E |
| 31 | D |
| 37 | V |
| 61 | G |
| 81 | M |
| 82 | E |
| 84 | S |

In an additional embodiment, at least the following amino acids in the heavy chain variable region that differ from SEQ ID NO: 7:

| Position relative to SEQ ID NO: 7 | Amino Acid |
|---|---|
| 37 | V |
| 81 | M |
| 82 | E |
| 84 | S |

In a further embodiment, the antibody or functional part comprises at least the following amino acids in the heavy chain variable region that differ from SEQ ID NO: 7:

| Position relative to SEQ ID NO: 7 | Amino Acid |
|---|---|
| 37 | V |
| 45 | L |
| 81 | M |
| 82 | E |
| 84 | S |

In an additional embodiment, the antibody or functional part comprises at least the following amino acids in the heavy chain variable region that differ from SEQ ID NO: 7:

| Position relative to SEQ ID NO: 7 | Amino Acid |
|---|---|
| 19 | K |
| 23 | K |
| 28 | T |
| 29 | F |
| 30 | S |
| 37 | V |
| 45 | L |
| 81 | M |
| 82 | E |
| 84 | S |

In a further embodiment, the antibody or functional part comprises at least the following amino acids in the heavy chain variable region that differ from SEQ ID NO: 7:

| Position relative to SEQ ID NO: 7 | Amino Acid |
|---|---|
| 30 | E |
| 31 | D |
| 37 | V |
| 61 | G |
| 81 | M |
| 82 | E |
| 84 | S |

In an additional embodiment, the antibody or functional part comprises the following amino acids in the heavy chain variable region that differ from SEQ ID NO: 7:

| Position relative to SEQ ID NO: 7 | Amino Acid |
|---|---|
| 30 | E |
| 31 | D |
| 37 | V |
| 61 | G |
| 81 | M |
| 82 | E |
| 84 | S |
| 109 | R |

In an additional embodiment, the antibody or functional part comprises at least the following amino acids in the heavy chain variable region that differ from SEQ ID NO: 7:

| Position relative to SEQ ID NO: 7 | Amino Acid |
|---|---|
| 19 | K |
| 23 | K |
| 28 | L |
| 30 | E |
| 31 | D |
| 37 | V |
| 61 | G |
| 77 | S |
| 81 | M |
| 84 | S |
| 98 | R |

In an additional embodiment, the antibody or functional part comprises at least the following amino acids in the heavy chain variable region that differ from SEQ ID NO: 7:

| Position relative to SEQ ID NO: 7 | Amino Acid |
|---|---|
| 19 | K |
| 23 | K |
| 28 | L |
| 30 | E |
| 31 | D |
| 37 | V |
| 61 | G |
| 81 | M |
| 84 | S |

In a further embodiment, the antibody or functional part comprises at least the following amino acids in the heavy chain variable region that differ from SEQ ID NO: 7:

| Position relative to SEQ ID NO: 7 | Amino Acid |
|---|---|
| 19 | K |
| 23 | K |
| 28 | L |
| 30 | E |
| 31 | D |
| 37 | V |
| 61 | G |
| 77 | S |
| 81 | M |
| 82 | E |
| 84 | S |

In an additional embodiment, the antibody or functional part comprises at least the following amino acids in the heavy chain variable region that differ from SEQ ID NO: 7:

| Position relative to SEQ ID NO: 7 | Amino Acid |
|---|---|
| 19 | K |
| 23 | K |
| 28 | L |
| 30 | E |
| 31 | D |
| 37 | V |
| 61 | G |
| 77 | S |
| 81 | M |
| 84 | S |

In a further embodiment, the heavy chain variable region CDR1 sequence comprises a sequence which differs by one amino acid from either NYIIN (SEQ ID NO: 1) or DYIIN (SEQ ID NO: 9), the heavy chain variable region CDR2 sequence comprises a sequence which differs by one or two amino acids from GIIPVLGTVHYAPKFQG (SEQ ID NO: 2) or GIIPVLGTVHYGPKFQG (SEQ ID NO: 10), and/or the heavy chain variable region CDR3 sequence comprising a sequence which differs by one or two amino acids from ETALVVSTTYLPHYFDN (SEQ ID NO: 3) or ETALVVSTTYRPHYFDN (SEQ ID NO: 11).

In a further embodiment, the light chain variable region CDR1 sequence comprising a sequence which differs by one amino acid from QASQDIVNYLN (SEQ ID NO: 4), the light chain variable region CDR2 sequence comprising a sequence which differs by one amino acid from VASNLET (SEQ ID NO: 5), and/or the light chain variable region CDR3 comprises a sequence which differs by one amino acid from QQYDNLP (SEQ ID NO: 6).

In a further embodiment, the heavy chain variable region CDR1 sequence comprises NYIIN (SEQ ID NO: 1) or DYIIN (SEQ ID NO: 9), the heavy chain variable region CDR2 sequence comprises GIIPVLGTVHYAPKFQG (SEQ ID NO: 2) or GIIPVLGTVHYGPKFQG (SEQ ID NO: 10), and/or the heavy chain variable region CDR3 sequence comprises ETALVVSTTYLPHYFDN (SEQ ID NO: 3) or ETALVVSTTYRPHYFDN (SEQ ID NO: 11).

In an additional embodiment, the light chain variable region CDR1 sequence comprises QASQDIVNYLN (SEQ ID NO: 4), the light chain variable region CDR2 sequence comprises VASNLET (SEQ ID NO: 5), and/or the light chain variable region CDR3 comprises QQYDNLP (SEQ ID NO: 6).

In one embodiment, a synthetic, recombinant, or isolated antibody or functional part thereof capable of specifically binding to a RSV F antigen comprises:
 a. a heavy chain variable region CDR1 sequence comprising the amino acid sequence DYIIN (SEQ ID NO: 9), and
 b. a heavy chain variable region CDR2 sequence comprising the amino acid sequence GIIPVLGTVHYGPKFQG (SEQ ID NO: 10), and
 c. a heavy chain variable region CDR3 sequence comprising the amino acid sequence ETALVVSTTYRPHYFDN (SEQ ID NO: 11), and
 d. a light chain variable region CDR1 sequence comprising the amino acid sequence QASQDIVNYLN (SEQ ID NO: 4), and
 e. a light chain variable region CDR2 sequence comprising the amino acid sequence VASNLET (SEQ ID NO: 5), and
 f. a light chain variable region CDR3 comprising the amino acid sequence QQYDNLP (SEQ ID NO: 6).

In another embodiment, a synthetic, recombinant, or isolated antibody or a functional part thereof capable of specifically binding to a RSV F antigen comprises:
 a. a heavy chain variable region CDR1 sequence comprising the amino acid sequence DYIIN (SEQ ID NO: 9), and
 b. a heavy chain variable region CDR2 sequence comprising the amino acid sequence GIIPVLGTVHYGPKFQG (SEQ ID NO: 10), and
 c. a heavy chain variable region CDR3 sequence comprising the amino acid sequence ETALVVSTTYLPHYFDN (SEQ ID NO: 3), and
 d. a light chain variable region CDR1 sequence comprising the amino acid sequence QASQDIVNYLN (SEQ ID NO: 4), and
 e. a light chain variable region CDR2 sequence comprising the amino acid sequence VASNLET (SEQ ID NO: 5), and
 f. a light chain variable region CDR3 comprising the amino acid sequence QQYDNLP (SEQ ID NO: 6).

In a further embodiment, the antibody or functional part has an Fc region having Y at position 252Y, T at position 254T, and E at position 256, wherein the numbering corresponds to the EU index in Kabat.

In yet a further embodiment, a method of inhibiting RSV infection in a subject comprising administering the antibody or functional part described herein to the subject.

In yet a further embodiment, a synthetic, recombinant, or isolated nucleic acid sequence encodes the antibody or functional part described herein.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 1A is a representation of the sequence for the D25 heavy chain and the J heavy chain variant. FIG. 1B is a representation of the sequence for the L and LA heavy chain variants.

FIG. 2 is a representation of the sequence for the heavy chain of several optimized variants (1G7, 1F5, 2D10).

FIG. 3A and FIG. 3B are representations of the sequence for the heavy chain of four additional variants of the optimized variant 1G7. FIG. 3A is a representation of the variants 1G7-GLM and B12-1. FIG. 3B is a representation of the variants E3-5 and E9-2. The variants (1G7-GLM, B12-1, E3-5, and E9-2) were made to alter pI by incorporating germline residues.

FIG. 8A and FIG. 8B show the neutralization of both RSV A2 and RSV B9320 by various antibodies.

FIG. 9A and FIG. 9B show the epitope for binding of 1G7 as defined by monoclonal antibody resistant mutants.

FIG. 10 shows the results of a neutralization assay against clinical isolates of RSV.

DESCRIPTION OF THE SEQUENCES

Figure 4A:
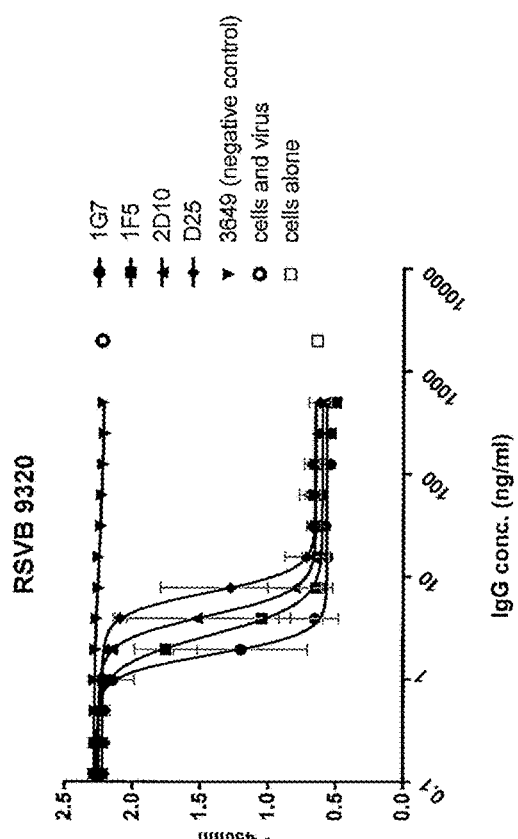
FIG. 4A and FIG. 4B show in vitro activity of D25 and several variants in a microneutralization assay.

Table 1 provides a listing of certain sequences referenced in present embodiments.

TABLE 1

| Description | Sequence | SEQ ID NO |
|---|---|---|
| D25 HC CDR1 | NYIIN | 1 |
| D25 HC CDR2 | GIIPVLGTVHYAPKFQG | 2 |
| D25 HC CDR3 | ETALVVSTTYLPHYFDN | 3 |
| D25 LC CDR1 | QASQDIVNYLN | 4 |
| D25 LC CDR2 | VASNLET | 5 |
| D25 LC CDR3 | QQYDNLP | 6 |
| D25 heavy chain variable region | QVQLVQSGAE VKKPGSSVMV SCQASGGPLR NYIINWLRQA PGQGPEWMGG IIPVLGTVHY APKFQGRVTI TADESTDTAY IHLISLRSED TAMYYCATET ALVVSTTYLP HYFDNWGQGT LVTVSS | 7 |
| D25 light chain variable region | DIQMTQSPSS LSAAVGDRVT ITCQASQDIV NYLNWYQQKP GKAPKLLIYV ASNLETGVPS RFSGSGSGTD FSLTISSLQP EDVATYYCQQ YDNLPLTFGG GTKVEIKRTV | 8 |
| Alternative HC CDR1 | DYIIN | 9 |
| Alternative HC CDR2 | GIIPVLGTVHYGPKFQG | 10 |
| Alternative HC CDR3 | ETALVVSTTYRPHYFDN | 11 |
| Alternative HC CDR3 | ETALVVSETYLPHYFDN | 22 |
| J variant heavy chain variable region | QVQLVQSGAE VKKPGSSVMV SCQASGGPLR NYIINWVRQA PGQGPEWMGG IIPVLGTVHY APKFQGRVTI TADESTDTAY MELSSLRSED TAMYYCATET ALVVSTTYLP HYFDNWGQGT LVTVSS | 12 |
| L variant heavy chain variable region | QVQLVQSGAE VKKPGSSVMV SCQASGGPLR NYIINWVRQA PGQGLEWMGG IIPVLGTVHY APKFQGRVTI TADESTDTAY MELSSLRSED TAMYYCATET ALVVSTTYLP HYFDNWGQGT LVTVSS | 13 |
| LA variant heavy chain variable region | QVQLVQSGAE VKKPGSSVKV SCKASGGTFS NYIINWVRQA PGQGLEWMGG IIPVLGTVHY APKFQGRVTI TADESTDTAY MELSSLRSED TAMYYCATET ALVVSTTYLP HYFDNWGQGT LVTVSS | 14 |
| Alternative heavy chain variable region | QVQLVQSGAE VKKPGSSVMV SCQASGGLLE DYIINWVRQA PGQGPEWMGG IIPVLGTVHY GPKFQGRVTI TADESTDTAY MELSSLRSED TAMYYCATET ALVVSTTYLP HYFDNWGQGT LVTVSS | 15 |
| 1G7 heavy chain variable region | QVQLVQSGAE VKKPGSSVMV SCQASGGLLE DYIINWVRQA PGQGPEWMGG IIPVLGTVHY GPKFQGRVTI TADESTDTAY MELSSLRSED TAMYYCATET ALVVSETYLP HYFDNWGQGT LVTVSS | 23 |

TABLE 1-continued

| Description | Sequence | SEQ ID NO |
|---|---|---|
| 1F5 heavy chain variable region | QVQLVQSGAE VKKPGSSVMV SCQASGGPLE DYIINWVRQA PGQGPEWMGG IIPVLGTVHY GPKFQGRVTI TADESTDTAY MELSSLRSED TAMYYCATET ALVVSTTYLP HYFDNWGQGT LVTVSS | 16 |
| 2D10 heavy chain variable region | QVQLVQSGAE VKKPGSSVMV SCQASGGPLE DYIINWVRQA PGQGPEWMGG IIPVLGTVHY GPKFQGRVTI TADESTDTAY MELSSLRSED TAMYYCATET ALVVSTTYRP HYFDNWGQGT LVTVSS | 17 |
| 1G7-GLM heavy chain variable region | QVQLVQSGAE VKKPGSSVKV SCKASGGLLE DYIINWVRQA PGQGPEWMGG IIPVLGTVHY GPKFQGRVTI TADESTSTAY MHLSSLRSED TAMYYCARET ALVVSTTYLP HYFDNWGQGT LVTVSS | 18 |
| B12-1 heavy chain variable region | QVQLVQSGAE VKKPGSSVKV SCKASGGLLE DYIINWVRQA PGQGPEWMGG IIPVLGTVHY GPKFQGRVTI TADESTDTAY MHLSSLRSED TAMYYCATET ALVVSTTYLP HYFDNWGQGT LVTVSS | 19 |
| E3-5 heavy chain variable region | QVQLVQSGAE VKKPGSSVKV SCKASGGLLE DYIINWVRQA PGQGPEWMGG IIPVLGTVHY GPKFQGRVTI TADESTSTAY MELSSLRSED TAMYYCATET ALVVSTTYLP HYFDNWGQGT LVTVSS | 20 |
| E9-2 heavy chain variable region | QVQLVQSGAE VKKPGSSVKV SCKASGGLLE DYIINWVRQA PGQGPEWMGG IIPVLGTVHY GPKFQGRVTI TADESTSTAY MHLSSLRSED TAMYYCATET ALVVSTTYLP HYFDNWGQGT LVTVSS | 21 |

DESCRIPTION OF THE EMBODIMENTS

I. Antibodies or Functional Parts Thereof

Improved RSV-specific antibodies or functional parts thereof having improved properties as compared to other antibodies are provided. Antibodies or functional parts, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

For example, the inventors have succeeded in generating RSV-specific antibodies with improved properties over prior RSV-specific antibodies, including improved protection against RSV A subtypes and RSV B subtypes, improved neutralization, and lower IC50 values. Such antibodies have a particular high or strong affinity for RSV and are therefore particularly suitable for counteracting and/or at least in part preventing an RSV infection and/or adverse effects of an RSV infection. Antibodies and functional parts thereof are synonymous with RSV-specific binding molecules and include any full length antibodies or antibody parts that are able to specifically bind RSV.

A. Antibodies or Functional Parts with Nongermline Residues Changed to Germline Residues In one embodiment, at least one nongermline residue of the heavy chain variable region of D25 (SEQ ID NO: 7) is changed to a germline residue. In another embodiment, at least 2, 3, 4, 5, 6, 7, 8, 9, 10, 11, or 12 nongermline residues of the heavy chain variable region of D25 residues are switched back to a germline residue. In a further embodiment, at least one nongermline residue may be changed to a germline residue and at least one CDR position may be modified relative to SEQ ID NO: 7.

One embodiment includes an isolated, synthetic, or recombinant antibody or a functional part thereof capable of specifically binding Respiratory Syncytial Virus and comprising:

a) a heavy chain CDR1 sequence comprising a sequence which is at least 70%, 75%, 80%, 85%, 90%, or 94% identical to the sequence NYIIN (SEQ ID NO: 1) or DYIIN (SEQ ID NO: 9), b) a heavy chain CDR2 sequence comprising a sequence which is at least 70%, 75%, 80%, 85%, 90%, or 94% identical to the sequence GIIPVLGTVHYAPKFQG (SEQ ID NO: 2) or GIIPVLGTVHYGPKFQG (SEQ ID NO: 10), c) a heavy chain CDR3 sequence comprising a sequence which is at least 70%, 75%, 80%, 85%, 90%, or 94% identical to the sequence ETALVVSTTYLPHYFDN (SEQ ID NO: 3) or ETALVVSTTYRPHYFDN (SEQ ID NO: 11), d) a light chain CDR1 sequence comprising a sequence which is at least 70%, 75%, 80%, 85%, 90%, or 94% identical to the sequence QASQDIVNYLN (SEQ ID NO: 4), e) a light chain CDR2 sequence comprising a sequence which is at least 70%, 75%, 80%, 85%, 90%, or 94% identical to the sequence VASNLET (SEQ ID NO: 5), and f) a light chain CDR3 sequence comprising a sequence which is at least 70%, 75%, 80%, 85%, 90%, or 94% identical to the sequence QQYDNLP (SEQ ID NO: 6).

and wherein at least one amino acid in the heavy chain differs from SEQ ID NO: 7 and said at least one amino acid is chosen from:

TABLE 2

| Position relative to SEQ ID NO: 7 | Type of Change | Amino Acid |
|---|---|---|
| 19 | nongermline framework changed to germline | K |
| 23 | nongermline framework changed to germline | K |
| 28 | nongermline framework changed to germline | T or L |
| 29 | nongermline framework changed to germline | F |
| 30 | nongermline framework changed to germline | S or E |
| 37 | nongermline framework changed to germline | V |
| 45 | nongermline framework changed to germline | L |
| 77 | nongermline framework changed to germline | S |
| 81 | nongermline framework changed to germline | M |
| 82 | nongermline framework changed to germline | E or H |
| 84 | nongermline framework changed to germline | S |
| 98 | nongermline framework changed to germline | R |

"At least one amino acid in the heavy chain variable region differs from SEQ ID NO: 7" means that the antibody or functional part must comprise at least one amino acid difference from SEQ ID NO: 7, although, in some embodiments, it may comprise more than one difference from SEQ ID NO: 7. In some embodiments it includes substitutions outlined in Table 2, deletions or alternative amino acids at positions listed in Table 2, or differences (including deletions, substitutions, or additions) in positions not listed in Table 2. Position numbers in Table 2 are provided relative to SEQ ID NO: 7 and the position number may not ultimately be the same as the position number based on the consecutive numbering of amino acids in the antibody or functional part of interest. Instead, position numbers are assigned based on alignment with SEQ ID NO: 7.

In one embodiment, the antibody or functional part includes a heavy chain and/or a light chain, wherein the heavy chain variable region is at least 90% identical to SEQ ID NO: 7 or SEQ ID NO: 15 and wherein the light chain variable region is at least 90% identical to SEQ ID NO: 8. In another embodiment, the heavy chain variable region is at least 91%, 92%, 93%, 94%, 95%, 96%, 97%, 98%, or 99% identical to SEQ ID NO: 7 or SEQ ID NO: 15. In another embodiment, the light chain variable region is at least 91%, 92%, 93%, 94%, 95%, 96%, 97%, 98%, or 99% identical to SEQ ID NO: 8.

In one embodiment, the antibody or functional part comprises a heavy chain variable region CDR1 sequence comprises a sequence which differs by one amino acid from either NYIIN (SEQ ID NO: 1) or DYIIN (SEQ ID NO: 9).

In one embodiment, the antibody or functional part comprises a heavy chain variable region CDR2 sequence comprises a sequence which differs by one or two amino acids from GIIPVLGTVHYAPKFQG (SEQ ID NO: 2) or GIIPVLGTVHYGPKFQG (SEQ ID NO: 10).

In one embodiment, the antibody or functional part comprises a heavy chain variable region CDR3 sequence comprising a sequence which differs by one or two amino acids from ETALVVSTTYLPHYFDN (SEQ ID NO: 3) or ETALVVSTTYRPHYFDN (SEQ ID NO: 11).

In one embodiment, the antibody or functional part comprises a light chain variable region CDR1 sequence comprising a sequence which differs by one amino acid from QASQDIVNYLN (SEQ ID NO: 4).

In one embodiment, the antibody or functional part comprises a light chain variable region CDR2 sequence comprising a sequence which differs by one amino acid from VASNLET (SEQ ID NO: 5).

In one embodiment, the antibody or functional part comprises a light chain variable region CDR3 comprises a sequence which differs by one amino acid from QQYDNLP (SEQ ID NO: 6).

In a further embodiment, the antibody or functional part comprises a heavy chain variable region CDR1 sequence comprising a sequence which differs by one amino acid from NYIIN (SEQ ID NO: 1) or DYIIN (SEQ ID NO: 9), a heavy chain variable region CDR2 sequence comprising a sequence which differs by one or two amino acids from GIIPVLGTVHYAPKFQG (SEQ ID NO: 2) or GIIPVLGTVHYGPKFQG (SEQ ID NO: 10), a heavy chain variable region CDR3 sequence comprising a sequence which differs by one or two amino acid from ETALVVSTTYLPHYFDN (SEQ ID NO: 3) or ETALVVSTTYRPHYFDN (SEQ ID NO: 11), a light chain variable region CDR1 sequence comprising a sequence which differs by one amino acid from QASQDIVNYLN (SEQ ID NO: 4), a light chain variable region CDR2 sequence comprising a sequence which differs by one amino acid from VASNLET (SEQ ID NO: 5), and/or a light chain variable region CDR3 sequence comprising a sequence which differs by one amino acid from QQYDNLP (SEQ ID NO: 6).

In some embodiments, the antibody or functional part comprises at least one or up to all of the identical CDRs as SEQ ID NO: 7 (heavy chain) and/or SEQ ID NO: 8 (light chain).

In one embodiment, the antibody or functional part comprises a heavy chain variable region CDR1 sequence comprising NYIIN (SEQ ID NO: 1) or DYIIN (SEQ ID NO: 9).

In one embodiment, the antibody or functional part comprises a heavy chain variable region CDR2 sequence comprising GIIPVLGTVHYAPKFQG (SEQ ID NO: 2) or GIIPVLGTVHYGPKFQG (SEQ ID NO: 10).

In one embodiment, the antibody or functional part comprises a heavy chain variable region CDR3 sequence comprising ETALVVSTTYLPHYFDN (SEQ ID NO: 3) or ETALVVSTTYRPHYFDN (SEQ ID NO: 11).

In another embodiment, the antibody of functional part comprises a heavy chain variable region CDR1 sequence comprising NYIIN (SEQ ID NO: 1) or DYIIN (SEQ ID NO: 9), a heavy chain variable region CDR2 sequence comprising GIIPVLGTVHYAPKFQG (SEQ ID NO: 2) or GIIPVLGTVHYGPKFQG (SEQ ID NO: 10), and/or a heavy chain variable region CDR3 sequence comprising ETALVVSTTYLPHYFDN (SEQ ID NO: 3) or ETALVVSTTYRPHYFDN (SEQ ID NO: 11).

In one embodiment, the antibody or functional part comprises a light chain variable region CDR1 sequence comprises QASQDIVNYLN (SEQ ID NO: 4).

In one embodiment, the antibody or functional part comprises a light chain variable region CDR2 sequence comprises VASNLET (SEQ ID NO: 5).

In one embodiment, the antibody or functional part comprises a light chain variable region CDR3 comprises QQYDNLP (SEQ ID NO: 6).

In another embodiment, the antibody of functional part comprises a light chain variable region CDR1 sequence comprises QASQDIVNYLN (SEQ ID NO: 4), a light chain variable region CDR2 sequence comprises VASNLET (SEQ ID NO: 5), and/or a light chain variable region CDR3 comprises QQYDNLP (SEQ ID NO: 6).

In a further embodiment, the antibody or functional part comprises a heavy chain variable region CDR1 sequence comprising NYIIN (SEQ ID NO: 1) or DYIIN (SEQ ID NO: 9), a heavy chain variable region CDR2 sequence comprising GIIPVLGTVHYAPKFQG (SEQ ID NO: 2) or GIIPVLGTVHYGPKFQG (SEQ ID NO: 10), a heavy chain variable region CDR3 sequence comprising ETALVVSTTYLPHYFDN (SEQ ID NO: 3) or ETALVVSTTYRPHYFDN (SEQ ID NO: 11), a light chain variable region CDR1 sequence comprising QASQDIVNYLN (SEQ ID NO: 4), a light chain variable region CDR2 sequence comprising VASNLET (SEQ ID NO: 5), and/or a light chain variable region CDR3 sequence comprising QQYDNLP (SEQ ID NO: 6).

In one embodiment, the antibody or functional part comprises a heavy chain variable region comprising a sequence which is 95% identical in the framework regions to a sequence chosen from SEQ ID NO: 12-21.

In one embodiment, the antibody or functional part comprises a heavy chain variable region comprising a sequence which is identical in the framework regions to a sequence chosen from SEQ ID NO: 12-21.

In one embodiment, the antibody or functional part comprises at least the following amino acids in the heavy chain variable region that differ from SEQ ID NO: 7:

TABLE 3

| J Variant | |
|---|---|
| Position relative to SEQ ID NO: 7 | Amino Acid |
| 37 | V |
| 81 | M |
| 82 | E |
| 84 | S |

In another embodiment, the differences provided in Table 3 are the only differences from SEQ ID NO: 7. In one embodiment, the differences provided in Table 3 are not the only differences from SEQ ID NO: 7. In another embodiment, the light chain variable region comprises SEQ ID NO: 8.

In one embodiment, the antibody or functional part comprises at least the following amino acids in the heavy chain variable region that differ from SEQ ID NO: 7:

TABLE 4

| L Variant | |
|---|---|
| Position relative to SEQ ID NO: 7 | Amino Acid |
| 37 | V |
| 45 | L |
| 81 | M |
| 82 | E |
| 84 | S |

In another embodiment, the differences provided in Table 4 are the only differences from SEQ ID NO: 7. In one embodiment, the differences provided in Table 4 are not the only differences from SEQ ID NO: 7. In another embodiment, the light chain variable region comprises SEQ ID NO: 8.

In one embodiment, the antibody or functional part comprises at least the following amino acids in the heavy chain variable region that differ from SEQ ID NO: 7:

TABLE 5

| LA Variant | |
|---|---|
| Position relative to SEQ ID NO: 7 | Amino Acid |
| 19 | K |
| 23 | K |
| 28 | T |
| 29 | F |
| 30 | S |
| 37 | V |
| 45 | L |
| 81 | M |
| 82 | E |
| 84 | S |

In another embodiment, the differences provided in Table 5 are the only differences from SEQ ID NO: 7. In one embodiment, the differences provided in Table 5 are not the only differences from SEQ ID NO: 7. In another embodiment, the light chain variable region comprises SEQ ID NO: 8.

In one embodiment, the antibody or functional part comprises at least the following amino acids in the heavy chain variable region that differ from SEQ ID NO: 7:

TABLE 6

| Alternative VH | |
|---|---|
| Position relative to SEQ ID NO: 7 | Amino Acid |
| 28 | L |
| 30 | E |
| 31 | D |
| 37 | V |
| 61 | G |
| 81 | M |
| 82 | E |
| 84 | S |

In another embodiment, the differences provided in Table 6 are the only differences from SEQ ID NO: 7. In one embodiment, the differences provided in Table 6 are not the only differences from SEQ ID NO: 7. In another embodiment, the light chain variable region comprises SEQ ID NO: 8.

In one embodiment, the antibody or functional part comprises at least the following amino acids in the heavy chain variable region that differ from SEQ ID NO: 7:

TABLE 7

| 1F5 | |
|---|---|
| Position relative to SEQ ID NO: 7 | Amino Acid |
| 30 | E |
| 31 | D |
| 37 | V |
| 61 | G |
| 81 | M |
| 82 | E |
| 84 | S |

In another embodiment, the differences provided in Table 7 are the only differences from SEQ ID NO: 7. In one embodiment, the differences provided in Table 7 are not the only differences from SEQ ID NO: 7. In another embodiment, the light chain variable region comprises SEQ ID NO: 8.

In one embodiment, the antibody or functional part comprises at least the following amino acids in the heavy chain variable region that differ from SEQ ID NO: 7:

TABLE 8

| 2D10 | |
|---|---|
| Position relative to SEQ ID NO: 7 | Amino Acid |
| 30 | E |
| 31 | D |
| 37 | V |
| 61 | G |
| 81 | M |
| 82 | E |
| 84 | S |
| 109 | R |

In another embodiment, the differences provided in Table 8 are the only differences from SEQ ID NO: 7. In one embodiment, the differences provided in Table 8 are not the only differences from SEQ ID NO: 7. In another embodiment, the light chain variable region comprises SEQ ID NO: 8.

In one embodiment, the antibody or functional part comprises at least the following amino acids in the heavy chain variable region that differ from SEQ ID NO: 7.

TABLE 9

| 1G7-GLM | |
|---|---|
| Position relative to SEQ ID NO: 7 | Amino Acid |
| 19 | K |
| 23 | K |
| 28 | L |
| 30 | E |
| 31 | D |
| 37 | V |
| 61 | G |
| 77 | S |
| 81 | M |
| 84 | S |
| 98 | R |

In another embodiment, the differences provided in Table 9 are the only differences from SEQ ID NO: 7. In one embodiment, the differences provided in Table 9 are not the only differences from SEQ ID NO: 7. In another embodiment, the light chain variable region comprises SEQ ID NO: 8.

In one embodiment, the antibody or functional part comprises at least the following amino acids in the heavy chain variable region that differ from SEQ ID NO: 7:

TABLE 10

| B12-1 | |
|---|---|
| Position relative to SEQ ID NO: 7 | Amino Acid |
| 19 | K |
| 23 | K |
| 28 | L |
| 30 | E |
| 31 | D |
| 37 | V |
| 61 | G |
| 81 | M |
| 84 | S |

In another embodiment, the differences provided in Table 10 are the only differences from SEQ ID NO: 7. In one embodiment, the differences provided in Table 10 are not the only differences from SEQ ID NO: 7. In another embodiment, the light chain variable region comprises SEQ ID NO: 8.

In one embodiment, the antibody or functional part comprises at least the following amino acids in the heavy chain variable region that differ from SEQ ID NO: 7:

TABLE 11

| E3-5 | |
|---|---|
| Position relative to SEQ ID NO: 7 | Amino Acid |
| 19 | K |
| 23 | K |
| 28 | L |
| 30 | E |
| 31 | D |
| 37 | V |
| 61 | G |
| 77 | S |
| 81 | M |
| 82 | E |
| 84 | S |

In another embodiment, the differences provided in Table 11 are the only differences from SEQ ID NO: 7. In one embodiment, the differences provided in Table 11 are not the only differences from SEQ ID NO: 7. In another embodiment, the light chain variable region comprises SEQ ID NO: 8.

In one embodiment, the antibody or functional part comprises at least the following amino acids in the heavy chain variable region that differ from SEQ ID NO: 7:

TABLE 12

| E9-2 | |
|---|---|
| Position relative to SEQ ID NO: 7 | Amino Acid |
| 19 | K |
| 23 | K |
| 28 | L |
| 30 | E |
| 31 | D |
| 37 | V |
| 61 | G |
| 77 | S |
| 81 | M |
| 84 | S |

In another embodiment, the differences provided in Table 12 are the only differences from SEQ ID NO: 7. In one embodiment, the differences provided in Table 12 are not the only differences from SEQ ID NO: 7. In another embodiment, the light chain variable region comprises SEQ ID NO: 8.

In one embodiment, the antibody or functional part comprises a heavy chain variable region sequence comprising a sequence which is at least 70%, 80%, 85%, 90%, 95%, 96%, 97%, 98%, 99%, or 100% identical to the sequence of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21. In another embodiment, the antibody or functional part comprises a heavy chain sequence variable region comprising a sequence which is at least 70%, 80%, 85%, 90%, 95%, 96%, 97%, 98%, 99%, or 100% identical to the framework (i.e., non CDR) sequence of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, or SEQ ID NO: 21.

In another embodiment, the antibody or functional part comprises a light chain variable region sequence comprising a sequence which is at least 70%, 80%, 85%, 90%, 95%, 96%, 97%, 98%, 99%, or 100% identical to the sequence DIQMTQSPSSLSAAVGDRVTIT CQASQDIVNYLNWY-QQKPGKAPKLLIYVASNLETGVPSRFSGSGSGTDFS-LTISSLQPED VATYYCQQYDNLPLTFGGGTKVE-IKRTV (SEQ ID NO: 8).

In other embodiments, conservative amino acid substitution is applied. Conservative amino acid substitution involves substitution of one amino acid with another with generally similar properties (size, hydrophobicity, etc.) such that the overall functioning is likely not to be seriously affected.

B. Antibodies or Functional Parts with Improved CDRs

In one embodiment, the antibody or functional part may comprise at least one CDR mutation relative to the CDRs present in SEQ ID NO: 7. In one embodiment, the antibody or functional part may comprise at least one of the changes in Table 13. In another embodiment, the antibody or functional part may comprise one, two, or all three of the changes in Table 13.

TABLE 13

| Position relative to SEQ ID NO: 7 | Type of Change | Amino Acid |
|---|---|---|
| 31 | CDR modification | D |
| 61 | CDR modification | G |
| 109 | CDR modification | R |

Another embodiment includes an isolated, synthetic, or recombinant antibody or a functional part thereof capable of specifically binding to a RSV F antigen and comprising a heavy chain variable region CDR1 sequence comprising the amino acid sequence DYIIN (SEQ ID NO: 9), a heavy chain variable region CDR2 sequence comprising the amino acid sequence GIIPVLGTVHYAPKFQG (SEQ ID NO: 2), a heavy chain variable region CDR3 sequence comprising the amino acid sequence ETALVVSTTYLPHYFDN (SEQ ID NO: 3), a light chain variable region CDR1 sequence comprising the amino acid sequence QASQDIVNYLN (SEQ ID NO: 4), a light chain variable region CDR2 sequence comprising the amino acid sequence VASNLET (SEQ ID NO: 5), and a light chain variable region CDR3 comprising the amino acid sequence QQYDNLP (SEQ ID NO: 6).

Another embodiment includes an isolated, synthetic, or recombinant antibody or a functional part thereof capable of specifically binding to a RSV F antigen and comprising a heavy chain variable region CDR1 sequence comprising the amino acid sequence NYIIN (SEQ ID NO: 1), a heavy chain variable region CDR2 sequence comprising the amino acid sequence GIIPVLGTVHYGPKFQG (SEQ ID NO: 10), a heavy chain variable region CDR3 sequence comprising the amino acid sequence ETALVVSTTYLPHYFDN (SEQ ID NO: 3), a light chain variable region CDR1 sequence comprising the amino acid sequence QASQDIVNYLN (SEQ ID NO: 4), a light chain variable region CDR2 sequence comprising the amino acid sequence VASNLET (SEQ ID NO: 5), and a light chain variable region CDR3 comprising the amino acid sequence QQYDNLP (SEQ ID NO: 6).

Another embodiment includes an isolated, synthetic, or recombinant antibody or a functional part thereof capable of specifically binding to a RSV F antigen and comprising a heavy chain variable region CDR1 sequence comprising the amino acid sequence NYIIN (SEQ ID NO: 1), a heavy chain variable region CDR2 sequence comprising the amino acid sequence GIIPVLGTVHYAPKFQG (SEQ ID NO: 2), a heavy chain variable region CDR3 sequence comprising the amino acid sequence ETALVVSTTYRPHYFDN (SEQ ID NO: 11), a light chain variable region CDR1 sequence comprising the amino acid sequence QASQDIVNYLN (SEQ ID NO: 4), a light chain variable region CDR2 sequence comprising the amino acid sequence VASNLET (SEQ ID NO: 5), and a light chain variable region CDR3 comprising the amino acid sequence QQYDNLP (SEQ ID NO: 6).

In another embodiment, an isolated, synthetic, or recombinant antibody or functional part thereof comprises a heavy chain variable region comprising heavy chain CDR1, CDR2, and CDR3 and a light chain comprising light chain CDR1, CDR2, and CDR3, wherein at least one, two, or all three of the heavy chain CDRs are chosen from column A, the remaining heavy chain CDRs (if any) are chosen from column B, and the light chain CDRs comprise column C in Table 14. Thus, in one embodiment, the light chain CDRs are provided in Table 14 column C and the heavy chain CDRs may be mixed-and-matched from columns A and B so long as the heavy chain has one of each of CDR1, CDR2, and CDR3.

TABLE 14

Alternative CDRs of One Set of Embodiments

| | A<br>Alternative<br>CDRs | B<br>D25 CDRs | C<br>Light Chain<br>CDRs |
|---|---|---|---|
| CDR1 | DYIIN<br>SEQ ID NO: 9) | NYIIN<br>(SEQ ID NO: 1) | QASQDIVNYLN<br>(SEQ ID NO: 4) |
| CDR2 | GIIPVLGTVHYGPK<br>FQG<br>(SEQ ID NO: 10) | GIIPVLGTVHYAPK<br>FQG,<br>(SEQ ID NO: 2) | VASNLET,<br>(SEQ ID NO: 5) |
| CDR3 | ETALVVSTTYRPHY<br>FDN<br>(SEQ ID NO: 11) | ETALVVSTTYLPHY<br>FDN,<br>(SEQ ID NO: 3) | QQYDNLP.<br>(SEQ ID NO: 6) |

The various alternative CDR embodiments do not necessarily contain any of the nongermline to germline mutations discussed above in section I.A, but any or all of those may optionally be present.

In one embodiment, the antibody or functional part may comprise at least one of the alternative heavy chain CDRs from Table 14 and may have at least one other CDR modification. Specifically, in yet another embodiment, the antibody or functional part may comprise a heavy chain CDR1 sequence comprising a sequence which differs by one amino acid from NYIIN (SEQ ID NO: 1), a heavy chain CDR2 sequence comprises a sequence which differs by one or two amino acids from GIIPVLGTVHYAPKFQG (SEQ ID NO: 2), a heavy chain CDR3 sequence comprises a sequence which differs by one or two amino acid from ETALVVSTTYLPHYFDN (SEQ ID NO: 3), a light chain CDR1 sequence comprises a sequence which differs by one amino acid from QASQDIVNYLN (SEQ ID NO: 4), a light chain CDR2 sequence comprises a sequence which differs by one amino acid from VASNLET (SEQ ID NO: 5), and/or a light chain CDR3 sequence comprises a sequence which differs by one amino acid from QQYDNLP (SEQ ID NO: 6), wherein at least one of heavy chain CDR1 is DYIIN SEQ ID NO: 9), heavy chain CDR2 is GIIPVLGTVHYGPKFQG (SEQ ID NO: 10), or heavy chain CDR3 is ETALVVST-TYRPHYFDN (SEQ ID NO: 11).

C. Antibodies or Functional Parts with Improved Half-Life

In one embodiment, additional modifications may be made to antibodies or functional parts described herein to improve their half-life. In one embodiment, mutations such as deletion, addition, or substitution mutations may be made to the antibodies or functional parts to improve their half-life. In one embodiment, the Fc region may be mutated to include one, two, or all three of the following substitutions M252Y, S254T, and T256E, wherein the numbering corresponds to the EU index in Kabat. In one embodiment, the Fc region may be mutated to include all of the following substitutions M252Y, S254T, and T256E, wherein the numbering corresponds to the EU index in Kabat. Dall'Acqua et al., Properties of Human IgG1s Engineered for Enhanced Binding to the Neonatal Fc Receptor (FcRn), J Biol Chem 281(33):23514-23524 (2006). The embodiment with all three substitutions is denoted as the YTE variant. Expressed differently, in one embodiment, the antibody or functional part has an Fc region having Y at position 252Y, T at position 254T, and E at position 256, wherein the numbering corresponds to the EU index in Kabat.

D. Other Characteristics of Antibodies and Functional Parts Thereof

In certain embodiment, the antibody or functional part has an IC50 value of less than 10 ng/ml in an in vitro neutralization assay wherein HEp-2 cells are infected with RSV and the antibody or functional part. In another embodiment, the IC50 is 9 ng/ml, 8 ng/ml, 7 ng/ml, 6 ng/ml, 5 ng/ml, 4 ng/ml, 3 ng/ml, or 2 ng/ml or less for RSV subtype A and/or RSV subtype B. In one embodiment, the IC50 is measured in the in vitro neutralization assay described in the examples, optionally for RSV A2 and/or RSV B9320.

In one embodiment, the antibodies and functional parts thereof are effective at neutralizing RSV subtype A strains. In one embodiment, the antibodies and functional parts thereof are effective at neutralizing RSV subtype B strains. In another embodiment, the antibodies and functional parts thereof are effective at neutralizing both RSV subtype A and B strains.

As used herein, the term antibody or functional part thereof is used in the broadest sense. It may be man-made such as monoclonal antibodies (mAbs) produced by conventional hybridoma technology, recombinant technology and/or a functional fragment thereof. It may include both intact immunoglobulin molecules for example a polyclonal antibody, a monoclonal antibody (mAb), a monospecific antibody, a bispecific antibody, a polyspecific antibody, a human antibody, a humanized antibody, an animal antibody (e.g. camelid antibody), chimeric antibodies, as well as portions, fragments, regions, peptides and derivatives thereof (provided by any known technique, such as, but not limited to, enzymatic cleavage, peptide synthesis, or recombinant techniques), such as, for example, immunoglobulin devoid of light chains, Fab, Fab', F (ab')$_2$, Fv, scFv, antibody fragment, diabody, Fd, CDR regions, or any portion or peptide sequence of the antibody that is capable of binding antigen or epitope. In one embodiment, the functional part is a single chain antibody, a single chain variable fragment (scFv), a Fab fragment, or a F(ab')$_2$ fragment.

An antibody or functional part is said to be "capable of binding" a molecule if it is capable of specifically reacting with the molecule to thereby bind the molecule to the antibody. Antibody fragments or portions may lack the Fc fragment of intact antibody, clear more rapidly from the circulation, and may have less non-specific tissue binding than an intact antibody. Examples of antibody may be produced from intact antibodies using methods well known in the art, for example by proteolytic cleavage with enzymes such as papain (to produce Fab fragments) or pepsin (to produce F(ab')$_2$ fragments). Portions of antibodies may be made by any of the above methods, or may be made by expressing a portion of the recombinant molecule. For example, the CDR region(s) of a recombinant antibody may be isolated and subcloned into an appropriate expression vector.

In one embodiment, an antibody or functional part is a human antibody. The use of human antibodies for human therapy may diminish the chance of side effects due to an immunological reaction in a human individual against non-human sequences. In another embodiment, the antibody or functional part is humanized. In another embodiment, an antibody or functional part is a chimeric antibody. This way, sequences of interest, such as for instance a binding site of interest, can be included into an antibody or functional part.

In one embodiment, the antibody may have an IgG, IgA, IgM, or IgE isotype. In one embodiment, the antibody is an IgG.

II. Nucleic Acids Encoding Antibodies and Functional Parts Thereof

The present embodiments further provides an isolated, synthetic, or recombinant nucleic acid sequence encoding any of the antibodies or functional parts described in section I.A or I.B above. Such nucleic acid is for instance isolated from a B-cell which is capable of producing an antibody or functional part. Such nucleic acids encode the heavy and light chain sequences set forth herein. Alternatively, such nucleic acids encode heavy and light chain sequences comprising the heavy and light chain CDRs, respectively, set forth herein. In some embodiments, the nucleic acids will encode functional parts of the antibodies described herein. Due to the degeneracy of the nucleic acid code, multiple nucleic acids will encode the same amino acid and all are encompassed herein.

III. Methods of Use

A. Methods of Use of Antibodies or Functional Parts

In one embodiment, an antibody or functional part may be used in a method of treatment or as a medicine. The method may be used for counteracting or at least in part preventing an RSV infection or for counteracting or at least in part preventing adverse effects of an RSV infection. The method also comprises administering to an individual in need thereof a therapeutically effective amount of an antibody or functional part as described herein. In one embodiment, the individual in need thereof is a human patient.

In one embodiment, in order to counteract RSV, an antibody or functional part may be administered to an individual before an RSV infection has taken place, in other words as a prophylactic agent. Alternatively, an antibody or functional part may be administered when an individual is already infected by RSV. Said antibody or functional part may be administered to individuals with an increased risk of RSV infection, such as for instance children with premature birth, individuals with chronic lung disease, congenital heart disease and/or compromised immunity, children with an age younger than 6 weeks. Children with premature birth include both infants in their first year of life, as well as children in their second year of life and older children who remain at risk of RSV infection. Also elderly people have an increased risk of RSV infection and thus may be targeted for administration based on risk. The antibodies or functional parts may also be administered to individuals who have had a prior RSV infection.

For therapeutic application, antibodies or functional parts are typically combined with a pharmaceutically acceptable carrier, adjuvant, diluent and/or excipient. In one embodiment, the antibodies or functional parts are combined with water for injection, In another embodiment, they are prepared in a sterile, preservative-free liquid solution with histidine, glycine, and chloride. In another embodiment, examples of suitable carriers for instance comprise keyhole limpet haemocyanin (KLH), serum albumin (e.g. BSA or RSA) and ovalbumin. In another embodiment, said suitable carrier comprises a solution like for example saline. In other embodiments, the antibodies or functional parts are provided in a lyophilized form and mixed with water for injection prior to administration.

B. Methods of Use of Nucleic Acids Encoding Antibodies or Functional Parts

In yet another embodiment a nucleic acid encoding an antibody or functional part may be administered. Upon administration of such nucleic acid, antibodies or functional parts are produced by the host's machinery. Produced antibodies or functional parts are capable of preventing and/or counteracting RSV infection and/or the adverse effects of an RSV infection.

A nucleic acid encoding a functional part of an antibody refers a nucleic acid at least 30 base pairs long, at least 50 base pairs long, or at least 100 base pairs long, comprising at least one expression characteristic (in kind not necessarily in amount) as a nucleic acid encoding an antibody. In one embodiment, a nucleic acid encoding a functional part of an antibody at least encodes an amino acid sequence comprising two or optionally three CDRs of the antibodies described herein.

IV. Methods of Making Antibodies and Functional Parts

An isolated antibody producing cell capable of producing an antibody or functional part is also provided. The antibodies or functional parts described herein may be manufactured from a hybridoma that secretes the antibody or from a recombinantly produced cell that has been transformed or transfected with a gene or genes encoding the antibody or functional part.

One embodiment includes a method of producing the antibody or functional part by culturing host cells under conditions wherein a nucleic acid is expressed to produce the antibody, followed by recovering the antibody. A variety of cell lines may be used for expressing the antibody or functional part, including, but not limited to, mammalian cell lines. In one embodiment, the cell lines may be human. In another embodiment, bacterial or insect cell lines may be used. In one embodiment, the cell lines include Chinese hamster ovary (CHO) cells, variants of CHO cells (for example DG44), 293 cells and NSO cells. In another embodiment, cell lines include VERY, BHK, Hela, COS, MDCK, 293F, 293T, 3T3, W138, BT483, Hs578T, HTB2, BT2O and T47D, CRL7O3O and HsS78Bst cells.

Recombinant expression utilizes construction of an expression vector containing a polynucleotide that encodes the antibody or functional part. Once a polynucleotide has been obtained, a vector for the production of the antibody may be produced by recombinant DNA technology well known in the art. Expression vectors may include appropriate transcriptional and translational control signals. This may be accomplished using in vitro recombinant DNA techniques, synthetic techniques, and in vivo genetic recombination. In one embodiment, a replicable vector comprises a nucleic acid sequence encoding an antibody or functional part operably linked to a heterologous promoter.

A variety of host-expression vector systems may be utilized to express antibodies or functional parts as described in U.S. Pat. No. 5,807,715. For example, mammalian cells such as Chinese hamster ovary cells (CHO), in conjunction with a vector such as the major intermediate early gene promoter element from human cytomegalovirus, are an effective expression system for antibodies (Foecking et al., Gene, 45:101 (1986); and Cockett et al., Bio/Technology, 8:2 (1990)). In addition, a host cell strain may be chosen which modulates the expression of inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the protein of the invention. To this end, eukaryotic host cells which possess the cellular machinery for proper processing of the primary transcript, glycosylation, and phosphorylation of the gene product may be used.

In bacterial systems, a number of expression vectors may be selected depending upon the use intended for the antibody or functional part being expressed. For example, when a large quantity of such an antibody or functional part is to be produced, for the generation of pharmaceutical compositions comprising an antibody or functional part, vectors which direct the expression of high levels of fusion protein products that are readily purified may be desirable. Such vectors include, but are not limited to, the *E. coli* expression vector pUR278 (Ruther et al., EMBO, 12:1791 (1983)), in which the coding sequence may be ligated individually into the vector in frame with the lac Z coding region so that a fusion protein is produced; pIN vectors (Inouye & Inouye, 1985, Nucleic Acids Res. 13:3101-3109 (1985); Van Heeke & Schuster, 1989, J. Biol. Chem., 24:5503-5509 (1989)); and the like. pGEX vectors may also be used to express foreign polypeptides as fusion proteins with glutathione-S-transferase (GST). In general, such fusion proteins are soluble and can easily be purified from lysed cells by adsorption and binding to glutathione-agarose affinity matrix followed by elution in the presence of free glutathione. The pGEX vectors are designed to introduce a thrombin and/or factor Xa protease cleavage sites into the expressed polypeptide so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The protein coding sequence may be cloned individually into non-essential regions (for example, the polyhedrin gene) of the virus and placed under control of an AcNPV promoter (for example, the polyhedrin promoter).

In mammalian host cells, a number of virus based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion into a non-essential region of the viral genome (e.g., region E1 or E3) will result in a recombinant virus that is viable and capable of expressing the antibody or functional part in infected hosts (e.g., see, Logan & Shenk, Proc. Natl. Acad. Sci. USA, 81:355-359 (1984)). Specific initiation signals may also be required for efficient translation of inserted antibody or functional part coding sequences. These signals include the ATG initiation codon and adjacent sequences. Furthermore, the initiation codon should generally be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol., 153:51-544 (1987)).

Stable expression can be used for long-term, high-yield production of recombinant proteins. For example, cell lines which stably express the protein molecule may be generated. Host cells can be transformed with an appropriately engineered vector comprising expression control elements (e.g., promoter, enhancer, transcription terminators, polyadenylation sites, etc.), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Plasmids that encode an antibody or functional part can be used to introduce the gene/cDNA into any cell line suitable for production in culture.

A number of selection systems may be used, including, but not limited to, the herpes simplex virus thymidine kinase (Wigler et al., Cell, 11:223 (1977)), hypoxanthineguanine phosphoribosyltransferase (Szybalska & Szybalski, Proc. Natl. Acad. Sci. USA, 48:202 (1992)), and adenine phosphoribosyltransferase (Lowy et al., Cell, 22:8-17 (1980)) genes can be employed in tk-, hgprt- or aprT-cells, respectively. Also, antimetabolite resistance can be used as the basis of selection for the following genes: dhfr, which confers resistance to methotrexate (Wigler et al., Natl. Acad. Sci. USA, 77:357 (1980); O'Hare et al., Proc. Natl. Acad. Sci. USA, 78:1527 (1981)); gpt, which confers resistance to mycophenolic acid (Mulligan & Berg, Proc. Natl. Acad. Sci. USA, 78:2072 (1981)); neo, which confers resistance to the aminoglycoside G-418 (Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIB TECH 11(5):155-2 15 (1993)); and hygro, which confers resistance to hygromycin (Santerre et al., Gene, 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds.), Current Protocols in Human Genetics, John Wiley & Sons, N Y (1994); Colberre-Garapin et al., 1981, J. Mol. Biol., 150:1.

Once an antibody or functional part has been produced by recombinant expression, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the proteins of the present invention or fragments thereof may be fused to heterologous polypeptide sequences described herein or otherwise known in the art to facilitate purification.

In some embodiments, RSV-specific antibody producing cells are generated which are stable for at least six months. In another embodiment, an RSV-specific antibody producing cell is stable for at least nine weeks, at least three months, or at least six months. In another embodiment, alternative methods of making antibodies and functional parts are well known in the art and described in at least U.S. Pat. No. 8,562,996.

Reference will now be made in detail to the present exemplary embodiments, examples of which are illustrated in the accompanying drawings. Wherever possible, the same reference numbers will be used throughout the drawings to refer to the same or like parts. Other embodiments will be apparent to those skilled in the art from consideration of the specification and practice disclosed herein. The embodiments are further explained in the following examples. These examples do not limit the scope of the claims, but merely serve to clarify certain embodiments. It is intended that the specification and examples be considered as exemplary only, with a true scope and spirit being indicated by the following claims.

EXAMPLES

Example 1. Preparation and Expression of Monoclonal Antibodies

The DNA fragments of 1G7 immunoglobulin variable light chain (VL) and variable heavy chain (VH), each containing desired mutations that improve the antibody's potency, were inserted into a human IgG1 expression vector containing the kappa light constant region and the CH1-hinge-CH2-CH3 IgG1 heavy constant region. To express 1G7 antibody, human embryonic kidney 293-F cells were transiently transfected with the 1G7-containing vector using 293Fectin™ reagent (Invitrogen, Carlsbad, Calif.). Cells were grown at 37° C., 120 rpm with 5% $CO_2$ and 80% humidity. The culture media was fed on the second day by adding equal volume media and harvested 10 days post transfection. The supernatant was sterile filtered to remove cells and debris. The IgG was purified using protein A column (Hi-trap protein A column, Sigma) and eluted protein was dialyzed against PBS overnight at 4° C. The IgG concentration was determined by protein quantitation in NanoDrop (Thermo Scientific).

The 1G7-containing vector RSV mAb 1G7 pOE was deposited with the American Type Culture Collection (ATCC®), 10801 University Boulevard, Manassas, Va. 20110-2209, USA under ATCC Patent Designation PTA-125140 on Sep. 21, 2018. This deposit is in accordance with the Budapest Treaty on the International Recognition of the Deposit of Microorganisms for the Purposes of Patent Procedure.

The same approach was taken to produce the other antibodies.

Example 2. In Vitro Microneutralization Assay

Microneutralization assays were performed as follows: Briefly, 2-fold serial dilutions of MAb were introduced into 384-well microtiter plates in HEp-2 cell culture medium at a volume of 15 μL/well. Subsequently, 15 μL of either RSV A2 or RSV B 9320 virus diluted into HEp-2 cell culture medium to concentration ranging from 80 to 150 pfu/well and was added to each well including control wells containing HEp-2 cell culture medium alone, and plates were incubated for 1.5 hours at 37° C. with 5% CO2. HEp-2 cells were added at $2.5 \times 10^5$ cells/mL in 30 μL to each well and the plates were incubated at 37° C. with 5% CO2. After 3 days for RSV A2 or 4 days for RSV B9320, medium was removed and 30 μL of ice cold 80% acetone/20% PBS was added to fix the cells.

Viral replication was measured by enzyme-linked immunosorbent assay (ELISA) using a horseradish peroxidase conjugated anti-RSV F MAb targeting the C site of RSV F (1331H) (Beeler and van Wyke Coelingh, J Virol. 63(7): 2941-2950 (1989). 1331H MAb was diluted 1:6,000 in PBS and 30 μl was added to each well. Following two hours of incubation at 37° C., the plates were washed three times with PBS-T. TMB peroxidase 30 μL was added to each well and the plates were incubated at room temperature in the dark for 15 minutes. The reaction was stopped by the addition of 15 μL of 2N H2SO4 to each well. Substrate turnover was measured by monitoring absorbance at 450 nm using a microplate reader. IC50 values were calculated using a non-linear fit algorithm in Graphpad Prism using the log (inhibitor) vs. response with variable slope curve fit and represent the concentration of MAb required for a 50% reduction in absorbance measured at 450 nm.

Figure 4B:
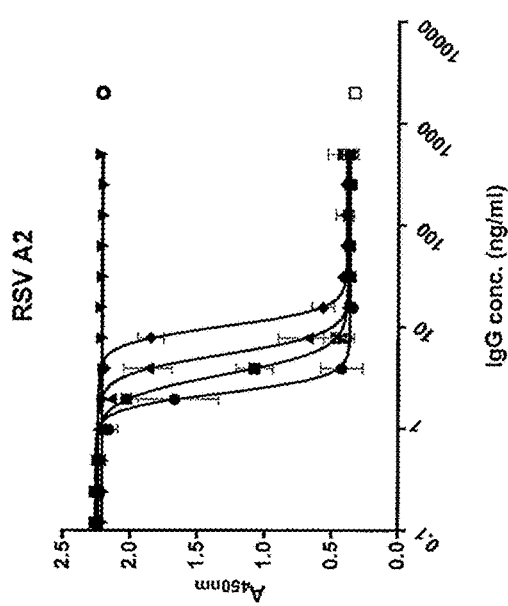

Results are provided in FIGS. 4A and 4B, which shows that 1G7, 1F5, 2D10, and D25 each inhibited RSV A2 and RSV B9320 replication in the microneutralization. 1G7 was the most effective, followed by 1F5, 2D10, and then D25.

Example 3. Cotton Rat RSV Model

A) Comparing the Ability of D25, J, L, and LA variants to Protect Against RSV Challenge Animals were dosed with 0.1 ml of antibody by intramuscular injection at the various dosage levels indicated in the figure. Twenty-four hours later, animals were anesthetized using an isoflourane chamber and infected by intranasal instillation of $1 \times 10^6$ pfu/animal of RSV strain A2. Four days later, animals were sacrificed by carbon dioxide asphyxiation; their lungs were surgically removed, bisected and frozen in liquid nitrogen or processed immediately. Blood samples were obtained by cardiac puncture at the time of sacrifice.

Figure 5A:
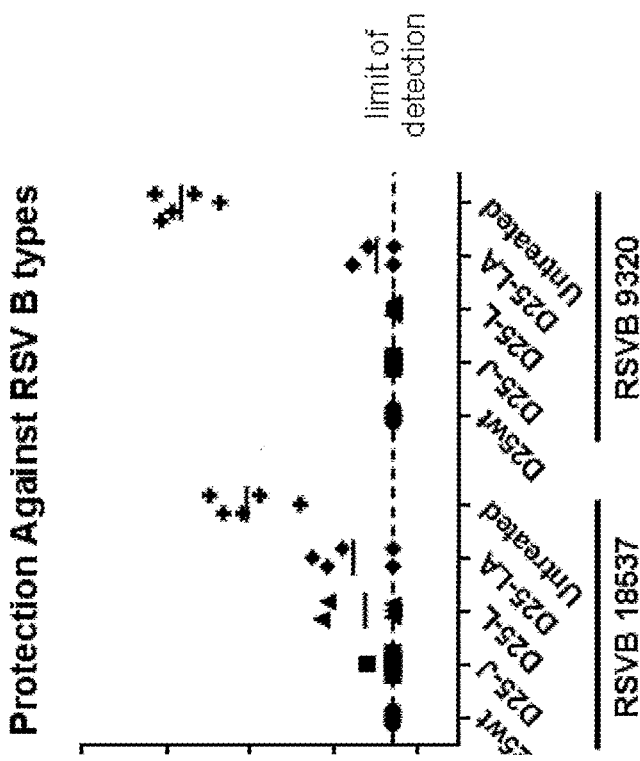
FIG. 5A and FIG. 5B show that D25 and several variants offer protection against RSV A2 and RSV B subtype challenge.
Figure 5B:
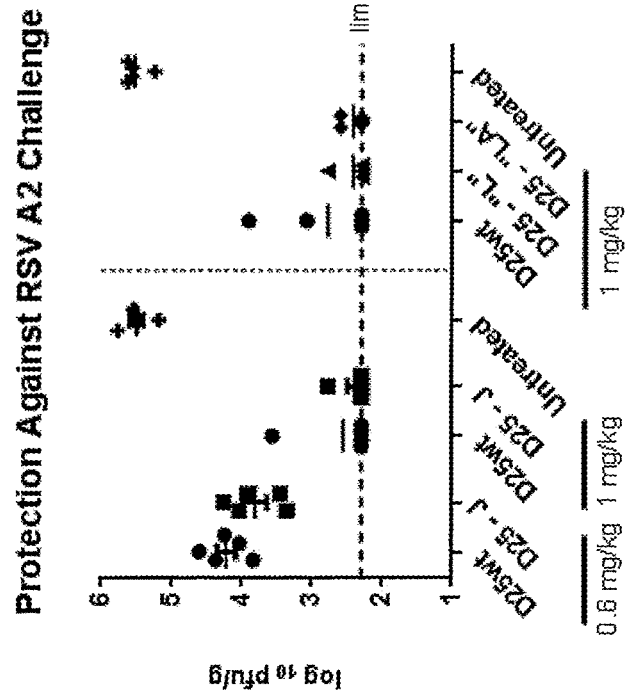

To assess the effect of MAb administration on RSV replication in the lungs of cotton rats, RSV viral titer in cotton rat lung homogenates were determined for each dose group. For that purpose, harvested lungs were individually homogenized in 10 parts (weight/volume) Hanks Balanced Salt Solution plus sucrose phosphate using a Fast Prep 24 tissue homogenizer for 20 seconds with TeenALysing Matrix tubes at room temperature. The resulting suspensions were centrifuged at 930×g for 10 min at 4° C., and the supernatants were collected and stored at −80° C. until analysis. Lung homogenate samples were diluted 1:10 and 1:100 in culture medium, and 50 μL of either undiluted lung homogenate or diluted lung homogenate samples were added to duplicate wells of HEp-2 cells that had been seeded at a cell density of $2.5 \times 10^5$ cells/well in 24-well plates, 24 hours prior to inoculation. After 1 hour incubation at 37° C. with 5% $CO_2$, the inoculum was replaced with culture medium containing 0.8% methylcellulose and the cells were incubated at 37° C. with 5% $CO_2$. Five days later the overlay was removed, and the cells were fixed and immuno-stained with an goat anti-RSV polyclonal antibody followed by a secondary anti-goat HRP antibody. Plaques were visualized by reaction with AEC reagent. Plaques were quantified under a microscope using a 10× objective. The limit of detection for this assay is 200 pfu/g of tissue. Samples with a viral titer below the limit of detection (<200 pfu/g) were designated at 100 pfu/g (one-half of the lower limit of detection) for purposes of the statistical analysis. Results are provided in FIGS. 5A and 5B, demonstrating that the J, L, and LA variants are all more effective than D25 in protecting against RSV A challenge, but that the L and LA variants were less effective in protecting against RSV B subtypes (with L performing better against one B strain than another). Based on this data, J was chosen as the starting point for further optimization.

Figure 6:
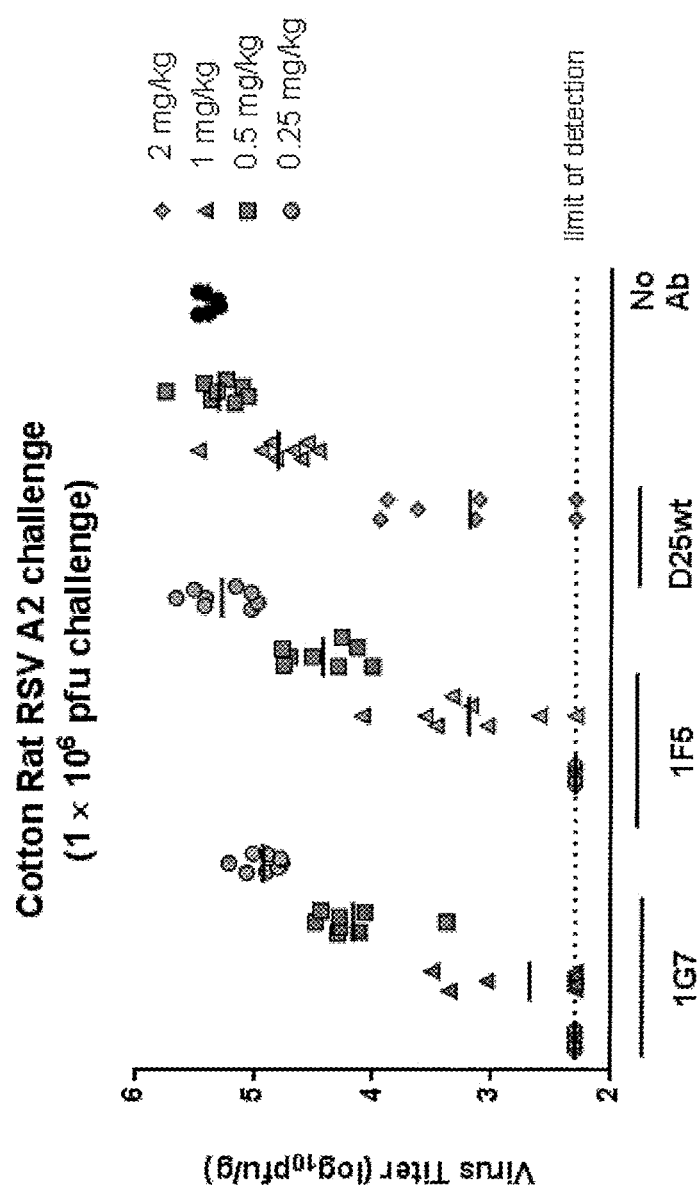
FIG. 6 shows the results of a cotton rat RSV A2 challenge in animals treated with 1G7, 1F5, D25 (designated in the figure as D25 wt), or no antibody.

B) Comparing the Ability of 1G7, 1F5, and D25 Variants to Protect Against RSV Challenge The model discussed above in part (A) of this example was used to compare the ability of 1G7, 1F5, and D25 to protect against RSV challenge. Animals were dosed at 2 mg/kg, 1 mg/kg, 0.5 mg/kg, and 0.25 mg/kg. Results are shown in FIG. 6. The data shows that 1G7 performed better than 1F5 in protecting against RSV challenge, though both were able to reduce the virus titer to the limit of detection. Both 1G7 and 1F5 performed better than D25.

C) Detailed Evaluation of 1G7 Variant

Figure 7A:
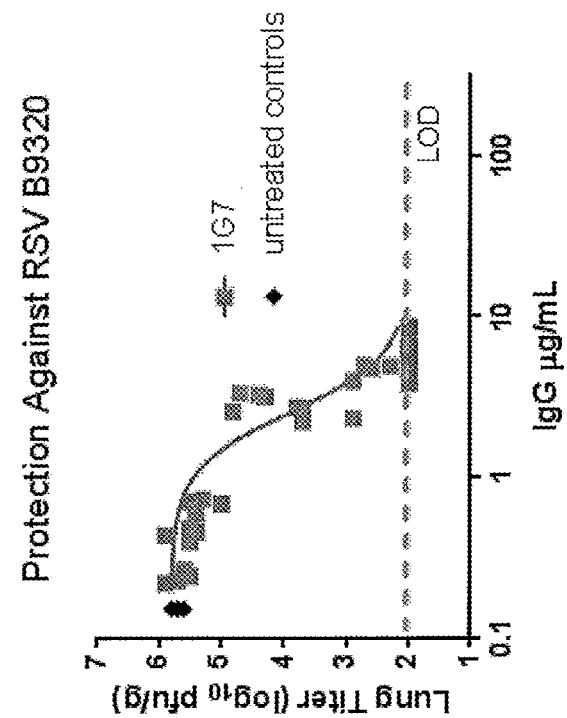
FIG. 7A and FIG. 7B show that 1G7 protects against both RSV A2 and RSV B9320. Lung titers of RSV are plotted as a function of the serum concentration of human IgG at the time of harvest.
Figure 7B:
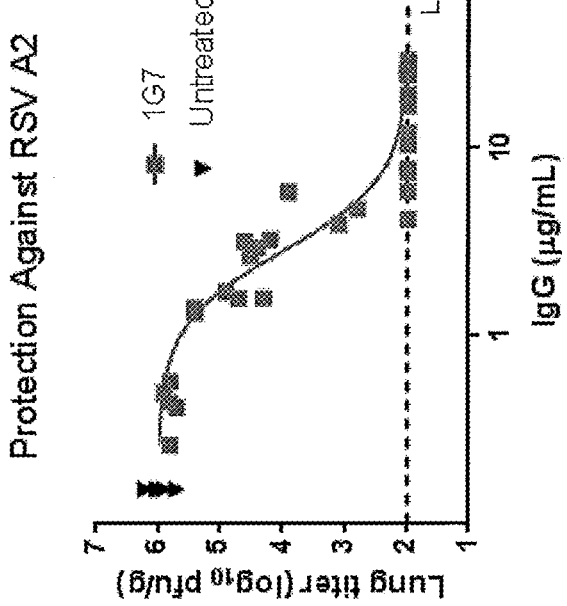

The same cotton rat model was used as described in section (A) above. Each animal received 0.1 ml of antibody, with varying concentrations of antibody present, as reported in FIGS. 7A and 7B. 1G7 demonstrates a dose-response relationship with RSV lung titer for both RSV A2 and RSV B9320.

D) Comparing the Ability of Variants to Neutralize RSV A2 and RSV B9320

The same cotton rat model was used as described in section (A) above.

The concentrations of human IgG in cotton rat serum samples on the day of lung harvest were determined using an ELISA method. In this assay the human antibodies were captured by a goat anti-human antibody bound to microtiter plates. The goat anti-human IgG (H+L) antibody (0.5 μg/mL in 1×PBS) was coated onto Nunc Maxisorp 384 well microtiter plates overnight at 4° C. in a 30 μL volume. Plates were washed then blocked with 60 μL of a solution of PBS+3% heat inactivated goat serum for 1 hour at room temperature. The blocking buffer was removed and samples were applied as follows: A two-fold serial dilution of the standard human antibody diluted in assay buffer was used for the standard curve with a concentration range of 500 ng/ml to 0.488 ng/ml. Standard curves were fitted using a 4 parameter curve fit.

Results are provided in FIGS. 8A and 8B, showing that the variants described herein have lower IC50s than D25 in neutralizing both RSV A2 and RSV B9320. This also demonstrates that there was no loss of activity against the A2 or B9320 virus with increased activity seen with E9-2 and B12-1 and only a nominal loss of activity against the B9320 virus with 1G7 GLM and E3-5.

Example 4. Epitope as Defined by Monoclonal Antibody Resistant Mutants

RSV A and RSV B virus mutants were isolated by passage three times in the presence of 250 ng/ml of 1G7-YTE. 1G7-YTE is the 1G7 antibody with the YTE mutation described above in section I.C above. Following the last passage the sequence of the RSV F protein was determined. Mutations correspond to regions that were previously defined in the co-crystal structure of RSV F with the parental D25 antibody. All resistant mutants contained changes in the region of RSV F protein in the F1 region between amino acids 200-213. Secondary mutations at position 294 were not shown to enhance resistance and were no more resistant than those with a single mutation in the region 200-213. Secondary mutations in the F2 region of the N2085 mutation background resulted in enhanced resistance. Results are provided in FIGS. 9A and 9B.

The 1G7-YTE antibody is encoded by the RSV mAb 1G7 pOE YTE vector, deposited with the American Type Culture Collection (ATCC), 10801 University Boulevard, Manassas, Va. 20110-2209, USA under ATCC Patent Designation PTA-125141 on Sep. 21, 2018. This deposit is in accordance with the Budapest Treaty on the International Recognition of the Deposit of Microorganisms for the Purposes of Patent Procedure.

Example 5. Neutralization Against Clinical Isolates of RSV

A neutralization assay was performed by pre-incubation of the expanded clinical isolate viruses with a dilution series of the antibodies prior to infection of HEp2 cells. Infection of cells was measured as a function of F protein expression on the surface of the cells. IC50 values were calculated by non-linear fitting of neutralization curves. Viral replication was measured as in Example 2 (In Vitro Microneutralization Assay).

Results are provided in FIG. 10. The IC50 for 1G7 and 1F5 are both lower than D25 for neutralizing either A isolates or B isolates of RSV in HEp2 cells.

INCORPORATION BY REFERENCE

All references cited herein, including patents, patent applications, papers, text books, and the like, and the references cited therein, to the extent that they are not already, are hereby incorporated herein by reference in their entirety for all purposes.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiments may be practiced in many ways and the claims include any equivalents thereof.

What is claimed is:

1. An antibody or antigen-binding fragment thereof, wherein the antibody or antigen-binding fragment thereof specifically binds Respiratory Syncytial Virus (RSV) and comprises:
 a heavy chain variable region which is at least 96% identical to SEQ ID NO:15 and a light chain variable region which is identical to SEQ ID NO: 8,
 wherein the heavy chain variable region CDR1 sequence comprises DYIIN (SEQ ID NO: 9), the heavy chain variable region CDR2 sequence comprises GIIPVLGTVHYGPKFQG (SEQ ID NO: 10), and the heavy chain variable region CDR3 sequence comprises a sequence which is identical to, or differs by one or two amino acids from, ETALVVSTTYRPHYFDN (SEQ ID NO: 11),
 wherein if the heavy chain variable region CDR3 sequence differs by one or two amino acids from ETALVVSTTYRPHYFDN (SEQ ID NO: 11), the differences are amino acid substitutions, and
 wherein the heavy chain variable region further comprises all of the following amino acids that differ from SEQ ID NO: 7:

| Position relative to SEQ ID NO: 7 | Amino Acid |
|---|---|
| 30 | E |
| 31 | D |
| 37 | V |
| 61 | G |
| 81 | M |

-continued

| Position relative to SEQ ID NO: 7 | Amino Acid |
|---|---|
| 82 | E |
| 84 | S. |

2. The antibody or antigen-binding fragment according to claim 1, comprising a heavy chain variable region which is at least 99% identical to SEQ ID NO:15.

3. The antibody or antigen-binding fragment according to claim 1 wherein the antibody or antigen-binding-fragment thereof comprises a human IgG1 isotype and comprises an Fc region comprising Y at position 252, T at position 254, and E at position 256, (EU numbering).

4. The antigen-binding fragment of claim 1, wherein the antigen-binding fragment thereof is a single chain antibody, a single chain variable fragment (scFv), a Fab fragment, or a F(ab')2 fragment.

5. A method of preventing or treating RSV infection in a subject, the method comprising administering the antibody or antigen-binding fragment thereof of claim 1 to the subject.

6. The method of claim 5, wherein the subject is a human subject.

7. The method of claim 6, wherein the human subject at an increased risk of RSV infection.

8. The method of claim 7, wherein the subject at an increased risk of RSV infection comprises children with premature birth, children with an age younger than 6 weeks, individuals with chronic lung disease, individuals with congenital heart disease, individuals with compromised immunity, or the elderly.

9. The antibody or antigen-binding fragment according to claim 1, wherein the heavy chain variable region CDR3 sequence comprises a sequence which differs by one amino acid from ETALVVSTTYRPHYFDN (SEQ ID NO: 11) and wherein the amino acid difference is an amino acid substitution.

10. The antibody or antigen-binding fragment according to claim 1, wherein the antibody or antigen-binding fragment is effective at neutralizing both RSV subtype A and B strains.

11. The antibody or antigen-binding fragment according to claim 1, wherein the heavy chain variable region CDR3 sequence comprises a sequence which differs by two amino acids from ETALVVSTTYRPHYFDN (SEG ID NO: 11) and wherein the amino acid difference is an amino acid substitution.

* * * * *

UNITED STATES PATENT AND TRADEMARK OFFICE
CERTIFICATE OF CORRECTION

PATENT NO. : 11,186,628 B2
APPLICATION NO. : 16/864454
DATED : November 30, 2021
INVENTOR(S) : Nancy Ulbrandt et al.

It is certified that error appears in the above-identified patent and that said Letters Patent is hereby corrected as shown below:

In the Claims

Claim 3, Column 43, Line 12, "antigen-binding-fragment" should read --antigen-binding fragment--.

Claim 3, Column 43, Line 15, "E at position 256, (EU numbering)" should read --E at position 256 (EU numbering)--.

Claim 7, Column 44, Lines 1-2, "wherein the human subject at an increased risk of RSV infection" should read --wherein the human subject is at an increased risk of RSV infection--.

Claim 11, Column 44, Line 22, "(SEG ID NO: 11)" should read --(SEQ ID NO: 11)--.

Signed and Sealed this
Nineteenth Day of December, 2023

Katherine Kelly Vidal
*Director of the United States Patent and Trademark Office*